US010058523B2

(12) United States Patent
Kelley

(10) Patent No.: US 10,058,523 B2
(45) Date of Patent: Aug. 28, 2018

(54) BENZOQUINONE DERIVATIVE E3330 IN COMBINATION WITH CHEMOTHERAPEUTIC AGENTS FOR THE TREATMENT OF CANCER AND ANGIOGENESIS

(71) Applicant: Indiana University Research and Technology Corporation, Indianapolis, IN (US)

(72) Inventor: Mark R. Kelley, Zionsville, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/690,973

(22) Filed: Apr. 20, 2015

(65) Prior Publication Data

US 2015/0265564 A1    Sep. 24, 2015

Related U.S. Application Data

(63) Continuation of application No. 12/679,824, filed as application No. PCT/US2008/077210 on Sep. 22, 2008, now Pat. No. 9,040,505.

(60) Provisional application No. 60/989,566, filed on Nov. 21, 2007, provisional application No. 60/975,396, filed on Sep. 26, 2007.

(51) Int. Cl.

| | |
|---|---|
| *A61K 31/201* | (2006.01) |
| *A61K 33/24* | (2006.01) |
| *A61K 31/7068* | (2006.01) |
| *A61K 31/198* | (2006.01) |
| *A61K 39/395* | (2006.01) |
| *A61K 31/454* | (2006.01) |
| *A61K 31/195* | (2006.01) |
| *A61K 45/06* | (2006.01) |
| *A61K 31/122* | (2006.01) |
| *A61K 31/13* | (2006.01) |
| *A61K 31/282* | (2006.01) |
| *A61K 31/203* | (2006.01) |

(52) U.S. Cl.
CPC .......... *A61K 31/201* (2013.01); *A61K 31/122* (2013.01); *A61K 31/13* (2013.01); *A61K 31/195* (2013.01); *A61K 31/198* (2013.01); *A61K 31/203* (2013.01); *A61K 31/282* (2013.01); *A61K 31/454* (2013.01); *A61K 31/7068* (2013.01); *A61K 33/24* (2013.01); *A61K 39/3955* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,210,239 A | 5/1993 | Abe et al. | |
| 5,849,793 A | 12/1998 | Pan et al. | |
| 5,919,643 A | 7/1999 | Kelley et al. | |
| 6,190,661 B1 | 2/2001 | Kelley et al. | |
| 6,235,756 B1* | 5/2001 | D'Amato | A61K 31/19 514/323 |
| 6,406,917 B1 | 6/2002 | Kelley et al. | |
| 2003/0091574 A1 | 5/2003 | Gevas et al. | |
| 2003/0229004 A1 | 12/2003 | Zarlilng et al. | |
| 2004/0002499 A1 | 1/2004 | Aggarwal | |
| 2005/0186208 A1 | 8/2005 | Fyfe et al. | |
| 2006/0024691 A1* | 2/2006 | Benz | A61K 31/138 435/6.14 |
| 2010/0297113 A1 | 11/2010 | Kelley et al. | |

FOREIGN PATENT DOCUMENTS

| | | |
|---|---|---|
| EP | 0813866 A2 | 12/1997 |
| JP | 07291859 | 7/1995 |
| WO | 200100229 A1 | 1/2001 |

OTHER PUBLICATIONS

Kakolyris et al. (British J. Cancer 1998 77(7): 1169-1173).*
Silvestris et al. (Int. J. Oncol. 2004 24:389-398).*
Fishel and Kelley (Molecular Aspects of Medicine May 3, 2007 28: 375-395) (Year: 2007).*
Luo et al. (Antioxidants & Redox Signaling Jul. 16, 2008 10 (11): 2008) (Year: 2008).*
Toschi et al. (Future Oncology 2005 1 (1): 7-17) (Year: 2005).*
Fayette, J., et al., Use of angiogenesis inhibitors in tumour treatment, European Journal of Cancer, 41/8, pp. 1109-1116, May 1, 2005.
Fishel, M., et al., The DNA base excision repair protein Ape1/Ref.-1 as a therapeutic and chemopreventative target, Molecular Aspects of Medicine, 28/3-4, pp. 375-395, Jun. 2007.
Gura, T., Systems for Identifying New Drugs Are Often Faulty, Science, vol. 278, No. 5340, pp. 1041-1042, Nov. 7, 1997.
Kaiser, J., First Pass at Cancer Genome Reveals Complex Landscape, Science, vol. 313, No. 5792, pp. 1370, Sep. 8, 2006.
Kelly et al., Abstracts, 36th Central Regional Meeting of the Amer. Chem. Soc., Jun. 2-4, 2004, Chem. Eng. News, vol. 82 (3), pp. 88, Jan. 19, 2004.
Database WPI Week 1996 Thomson Scientific, London, GB; AN 1996-017132 XP002508298 Goto Masaki Et al: "NFkB transcription factor inhibitor" -& JP 07 291859 A (EISAI Co Ltd) Nov. 7, 1995 (Nov. 7, 1995).

(Continued)

*Primary Examiner* — Peter J Reddig
(74) *Attorney, Agent, or Firm* — Stinson Leonard Street LLP

(57) ABSTRACT

Disclosed are novel methods for the therapeutic treatment of cancer and angiogenesis. The enzyme Ape1/Ref-1, via its redox function, enhances the DNA binding activity of transcription factors that are associated with the progression of cancer. The present invention describes the use of agents to selectively inhibit the redox function of Ape1/Ref-1 and thereby reduce tumor cell growth, survival, migration and metastasis. In addition, Ape1/Ref-1 inhibitory activity is shown to augment the therapeutic effects of other therapeutics and protect normal cells against toxicity. Further, Ape1/Ref-1 inhibition is shown to decrease angiogenesis, for use in the treatment of cancer as well other pathologic conditions of which altered angiogenesis is a component.

9 Claims, 35 Drawing Sheets

(56) References Cited

OTHER PUBLICATIONS

Mital, A., et al., Synthesis of novel 2-substituted 1,4-naphthoquinones using Heck reaction in 'green' reaction media Arkivoc Journal, vol. 11, No. ISSN:1424-6376, 2006, pp. 99-106.

Luo, M., et al., Inhibition of the human apuriniclapyrimidic endonuclease DNA base excision repair enzyme/redox factor (APE1/REF-1) using small molecule redox and repair inhibitors: Therapeutic implications, Proceedings of the Annual Meeting of the American Association for Cancer Research, 45/1, pp. 703-704, Mar. 1, 2004.

Macular degeneration, Wikipedia, the free encyclopedia, accessed on Dec. 16, 2013.

Proprionic Acid (MP Biomedicals™ 15698866—Chemical Product Phy. Prop Display—Fisher Scientific, 2014.

Proprionic Acid 79-09-4 (Chemical Book, htp://www.chemicalbook.com/ChemicalProductProperty_EN_CB4138567.htm, 2010.

Jiang, Y., et al., Implications of apurinic/apyrimidinic endonuclease in reactive oxygen signaling response after cisplatin treatment of dorsal root ganglion neurons, Cancer Research / American Association for Cancer Research, Philadelphia, PA. : AACR, vol. 68, No. 15, Aug. 1, 2008 (Aug. 1, 2008), pp. 6425-6434.

Reed, A., et al., Potentiation of melphalan-induced cytotoxicity through targeting of the base excision repair pathway in multiple myeloma, Blood, American Society of Hematology, US, vol. 110, No. 11, Part 2, Nov. 1, 2007 (Nov. 1, 2007), p. 273B.

Saitou Y, et al., (2005) Augmentation of tumor necrosis factor family-induced apoptosis by E3330 in human hepatocellular carcinoma cell lines via inhibition of NF kB. World Journal of Gastroenterolology 11 6258-6261.

E3330-PubChem (PubChem Compound http://pubchem.ncbi.nim.nih.gov/summary/summary.cgi?cid=6439397, Apr. 29, 2006.

Van Noort, JM., et al., Cell Biology of Autoimmune Diseases, Int Rev. Cytol., 1998, vol. 178, pp. 127-206.

Goto et al., Inhibitory Effect of E3330, a Novel quinine Derivative Able to Suppress Tumor Necrosis Factor-a Generation, on Activation of Nuclear Factor-kB, Molecular Pharmacology, 49:860-873, 1996.

Uetsuka et al., Protective Effects of a Novel Quinone Derivative, E3330, on Mouse Hepatitis Virus (MHV)-Induced Chronic Hepatitis In Athymic Nude Mice, Exp. Anim. 46(3): 219-223, Jul. 1997.

Donnem et al., Vessel Co-option in Primary Human Tumors and Metastases: An Obstacle to Effective Anti-Angiogenic Treatment?, Cancer Med. 2(4): 427-436, Aug. 2013.

Stessels et al., Breast Adenocarcinoma Liver Metastases, in Contrast to Colorectal Cancer Liver Metastases, Display a Non-Angiogenic Growth Pattern that Preserves the Stroma and Lacks Hypoxia, Br J Cancer, 90 (7):1429-1436, Apr. 5, 2004.

Evidence for Novel Non-Angiogenic Pathway in Breast-Cancer Metastasis, Lancet, 355(9217): 1787-1788, May 20, 2000, citing Abstract only.

Nanji et al., Protective Effects of a Novel Quinone Derivative, (2E)-3-[5-(2,3 dimethoxy-6-methyl-1,4-benzoquinoyl)]-2-nonyl-2-propanoic acid on Experimental Alcoholic Liver Injury, Journal of Pharmacology and Experimental Therapeutics, Aug. 1993, vol. 266, No. 2, pp. 1085-1090.

Silber et al., The Apurinic/Apyrimidinic Endonuclease Activity of Ape1/Ref-1 Contributes to Human Glioma Cell Resistance to Alkylating Agents and is Elevated by Oxidative Stress, Clinical Cancer Research, vol. 8, pp. 3008-3018, 2002.

* cited by examiner

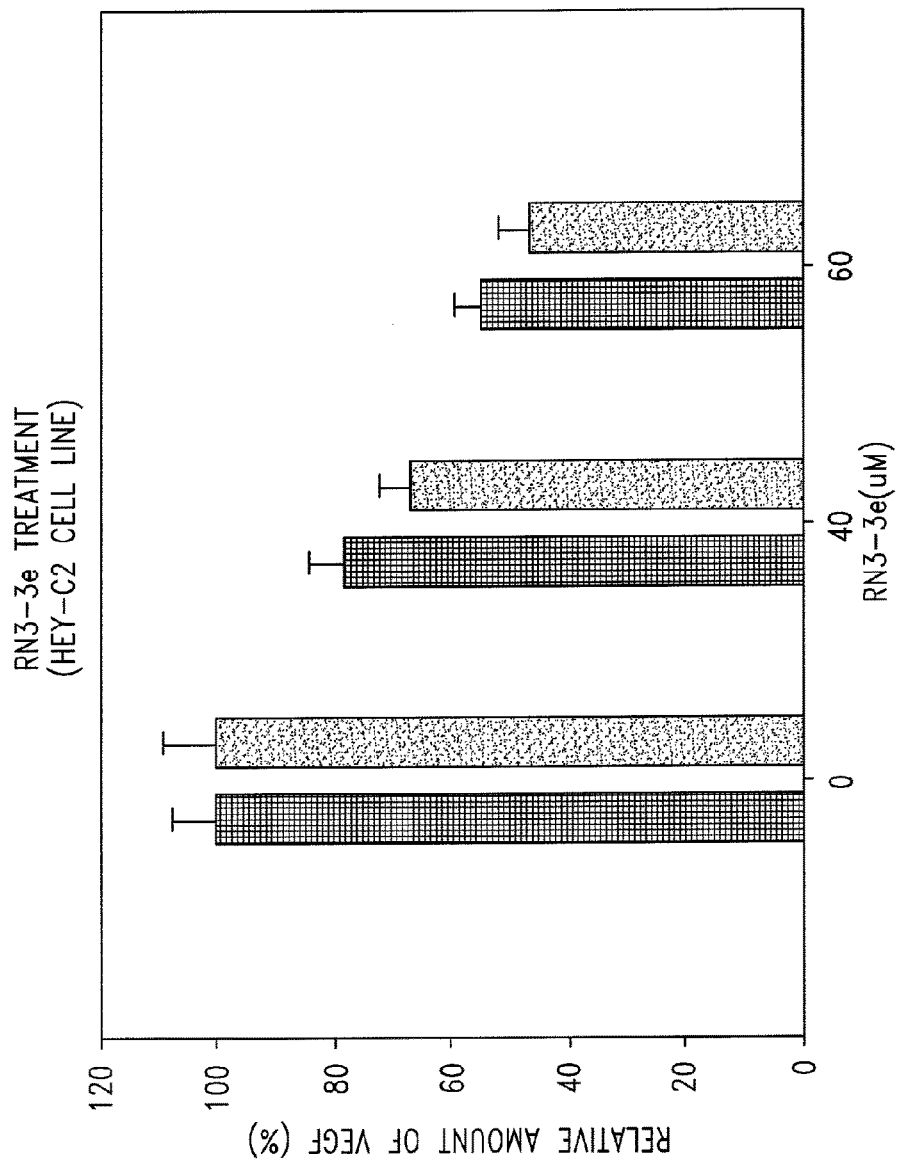

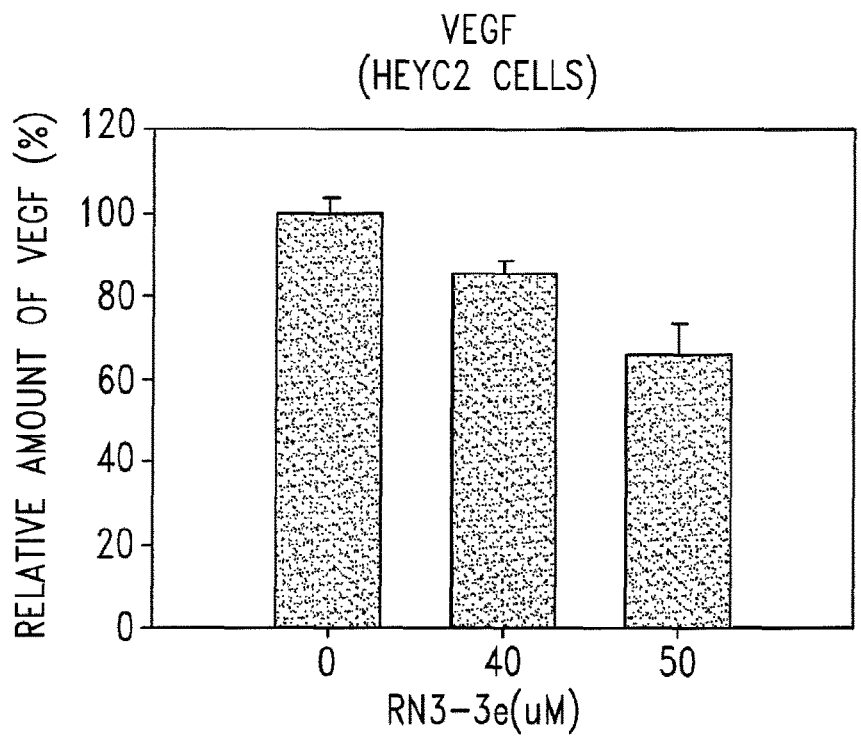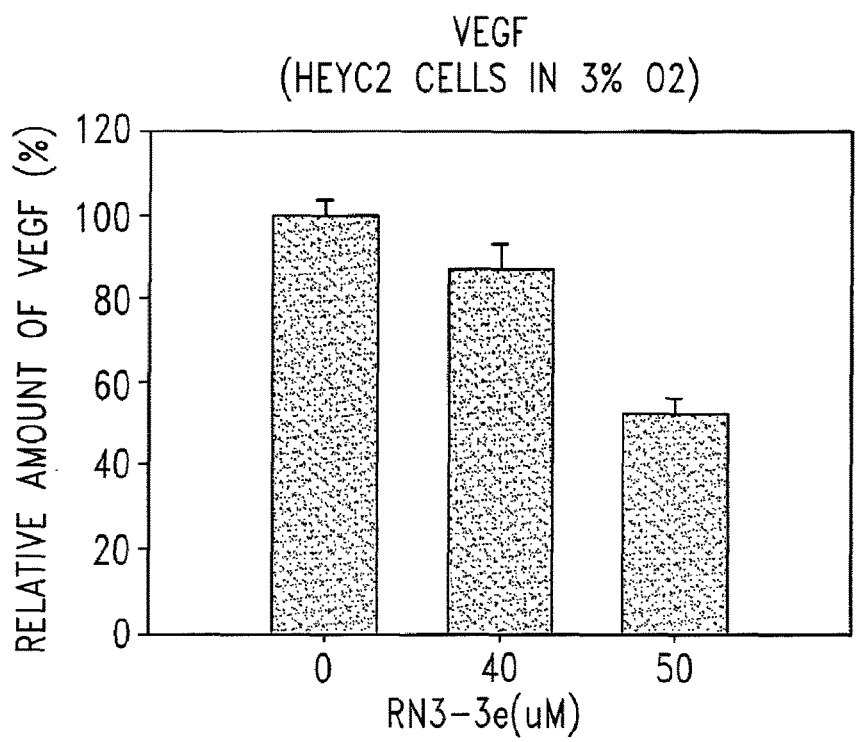
Fig. 3B

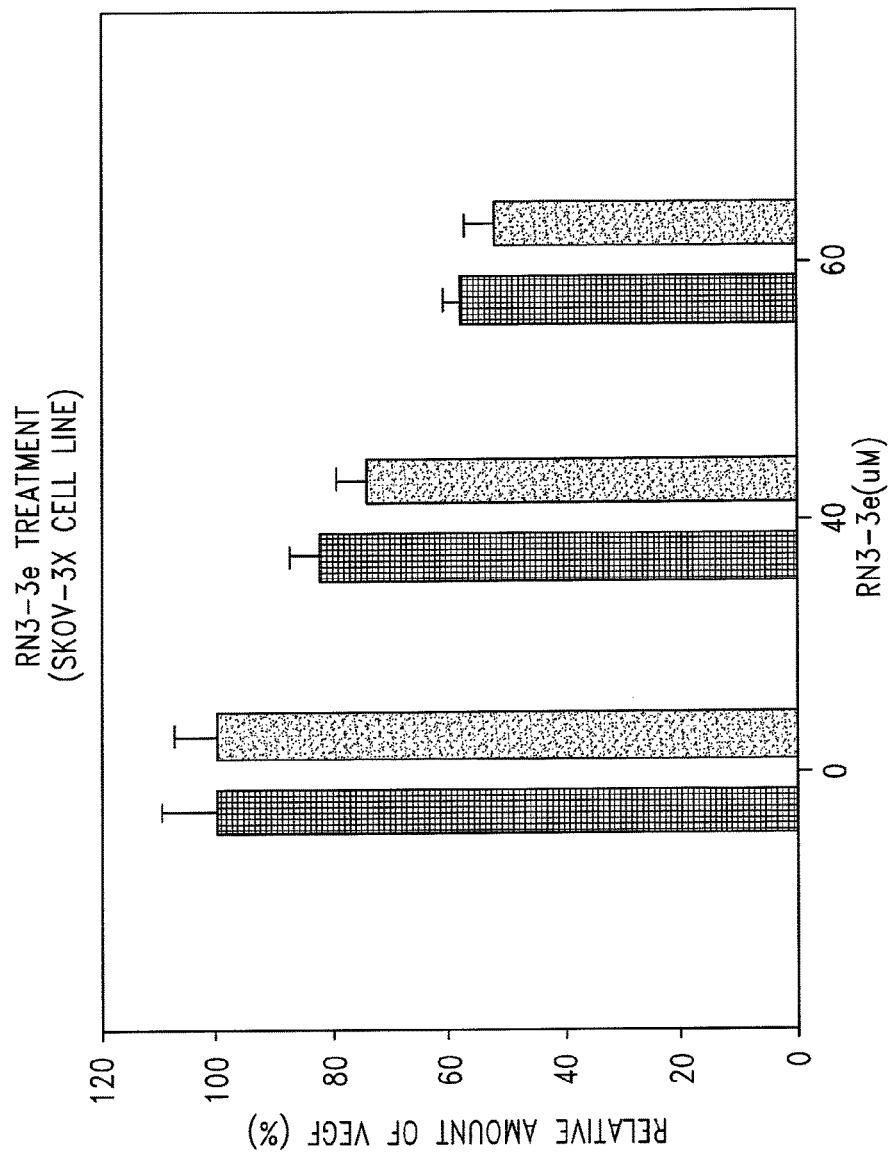

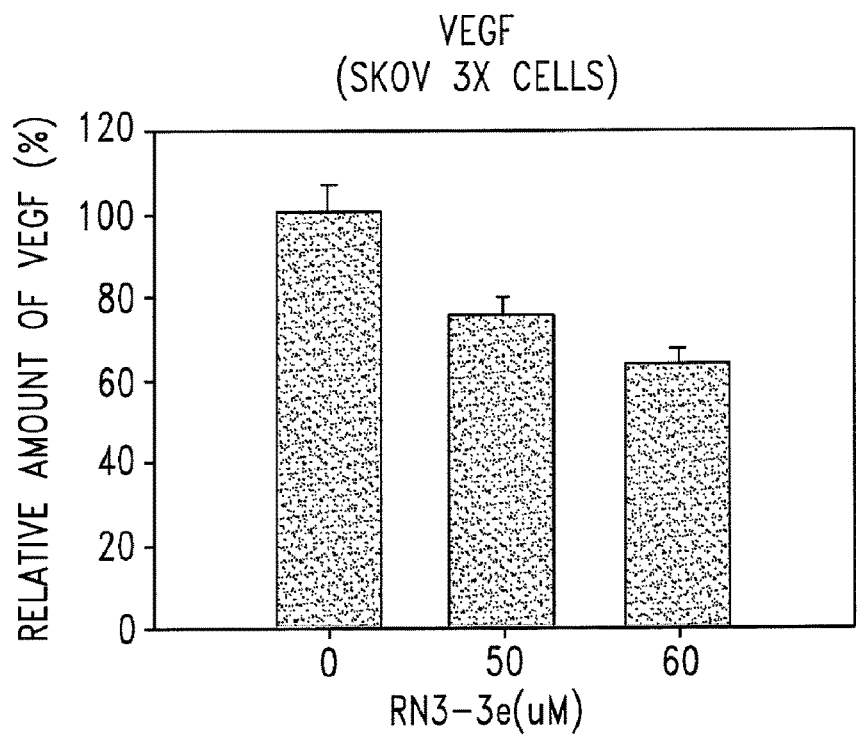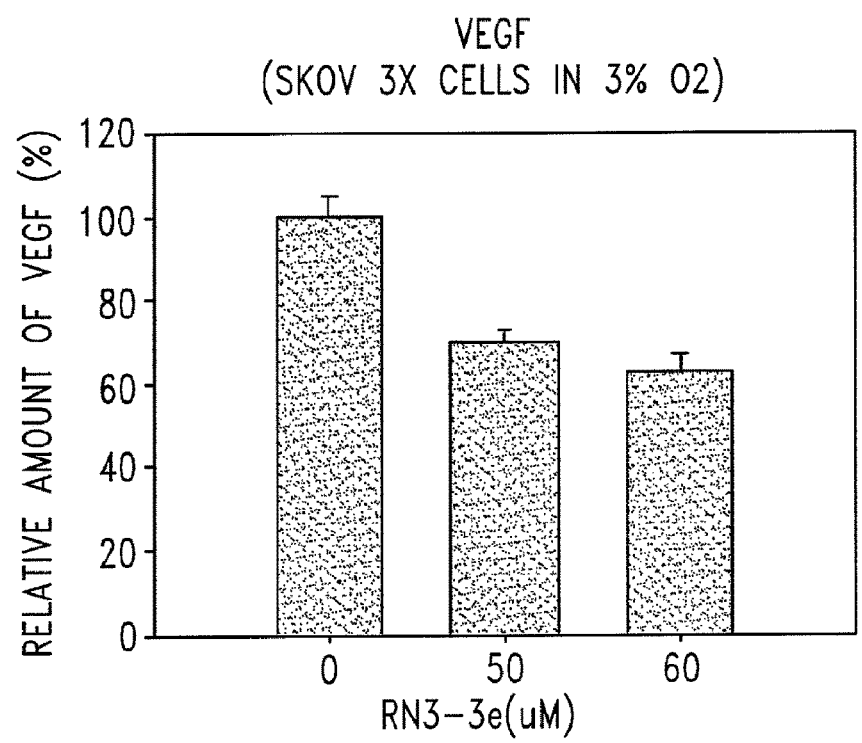
Fig. 4B

MTS PROLIFERATION ASSAY:

|  | EBM | EBM + bFGF |
|---|---|---|
| CONTROL | 100 ± 11.03467 | 177.41 |
| DMSO CONTROL | 62.41 ± 9.5616 | 144.47 ± 23.1686 |
| 10 µM E3330 | 26.85 ± 8.6409 | 74.01 ± 8.2798 |
| 25 µM 3330 | 6.586 ± 8.4687 | 1.861 ± 3.3570 |
| 50 µM 3330 | 14.84 ± 10.9869 | 2.448 ± 3.6067 |
| 100 µM 3330 | 7.713 ± 1.7757 | 3.462 ± 1.4779 |

P VALUE

|  | EBM | EBM + bFGF |
|---|---|---|
| DMSO-10 µM E3330 | 0.001489 | 0.001229 |
| DMSO-25 µM E3330 | 0.000124 | 0.000019 |
| DMSO-50 µM E3330 | <0.001 | <0.001 |
| DSMO-100 µM E3330 | <0.001 | <0.001 |
| 10 µM E3330 - 25 µM3330 | 0.006595 | 0.000003 |

Fig 10

| Survival | | | | | | |
|---|---|---|---|---|---|---|
| | | Day 2 | Day 3 | Day 4 | Day 5 | |
| Dose of E3330 | | 19 Sep | 20-Sep | 21-Sep | 22-Sep | |
| mg/kg | | | | | | |
| 0 | female | 4/4 | 4/4 | 4/4 | 4/4 | |
| | male | 4/4 | 4/4 | 4/4 | 4/4 | |
| 10 | female | 4/4 | 4/4 | 4/4 | 4/4 | |
| | male | 4/4 | 4/4 | 4/4 | 4/4 | |
| 25 | female | 4/4 | 3/4 | 3/4 | 3/4 | |
| | male | 4/4 | 4/4 | 4/4 | 4/4 | |
| 50 | female | 4/4 | 4/4 | 1/4 | 3/4 | |
| | male | 3/4 | 2/4 | 2/4 | 1/4 | |
| 100 | female | 0/6 | N/A | N/A | N/A | |
| | male | 0/1 | | | | |

Fig. 20

| Mouse Sample ID | Time (hrs) | E-3330 Peak Area | BMC Peak Area | Area Ratio | Estimated Conc. (ng/mL) | Std. Curve Range | μM | Cage # | Tail mark | Time | Sample ID |
|---|---|---|---|---|---|---|---|---|---|---|---|
| 2 | 0.5 | 1970000 | 41300 | 47.6998 | 2200 | 0-10000 | 5.8 | 371529 | 1 | 30 | 2 |
| 7 | 1 | 1230000 | 52000 | 23.6538 | 954 | | 2.5 | 371529 | 1111 | 60 | 7 |
| 12 | 2 | 1010000 | 21400 | 47.1963 | 2174 | | 5.7 | 371528 | 111 | 2 | 12 |
| 17 | 4 | 806000 | 52100 | 15.4702 | 476 | 0-3000 | 1.3 | 371529 | 1 | 4 | 17 |
| 22 | 8 | 73500 | 11100 | 6.6216 | 209 | | 0.6 | 371529 | 1111 | 8 | 22 |
| 27 | 24 | 18800 | 27300 | 0.6886 | 16 | 0-30 | 0.041 | 371528 | 111 | 24 | 27 |

Fig. 21A

| Group | lambda (hr-1) | t$_{1/2}$ (hr) | Dosage (mg) | Weight (kg) | AUC $_{0-Infinity}$ (hr*ng/mL) | Cl/F | | |
|---|---|---|---|---|---|---|---|---|
| | | | | | | mL/hr | L/hr | mL/min |
| All mice | 0.198 | 3.5 | 0.5181 | 0.0207 | 3789 | 136.72 | 0.137 | 2.3 |
| Female | 0.1988 | 3.5 | 0.483 | 0.0193 | 5691 | 84.86 | 0.085 | 1.4 |
| Male | 0.1919 | 3.6 | 0.578 | 0.0231 | 941 | 614.27 | 0.614 | 10.2 |
| Definition of Terms | | | | | | | | |
| t$_{1/2}$ is half-life | | | | | | | | |
| Cl/F is blood clearance divided by the bioavailability of the drug | | | | | | | | |

Fig. 22

EC3330 held constant and RA varying dosages

| CELLS | CD11 EXP 03607 day 4 | day 6 |
|---|---|---|
| WT HL60 EtOH | 7 | 4 |
| 25uM E3330 | 11 | 13 |
| 10-5M RA | 140 | 185 |
| 10-5M RA+25uM E3330 | 280 | 390 |
| 10-6M RA | 150 | 223 |
| 10-6M RA+25uM E3330 | 246 | 409 |
| 10-7M RA | 140 | 212 |
| 10-7M RA+25uM E3330 | 147 | 309 |
| 10-8M RA | 100 | 124 |
| 10-8M RA+25uM E3330 | 130 | 248 |
| 10-9M RA | 35 | 21 |
| 10-9M RA+25uM E3330 | 31 | 35 |

RA+E330 yields approximately a 2 fold increase in cellular differentiation compared to the same concentration of RA alone. You can achieve the same amount of differentiation with 1000 fold lower dose. (Compare numbers for 10-5M RA and 10-8M RA+25 uM E3330.)

Fig. 25

| CELLS | Annexin : (UR+LR) 03607 | |
|---|---|---|
| | Exp day4 | day6 |
| WT HL60 EtOH | 4 | 4 |
| 25uM E3330 | 7 | 15 |
| 10-5M RA | 15 | 37 |
| 10-5M RA+25uM E3330 | 28 | 66 |
| 10-6M RA | 15 | 36 |
| 10-6M RA+25uM E3330 | 18 | 50 |
| 10-7M RA | 15 | 27 |
| 10-7M RA+25uM E3330 | 14 | 34 |
| 10-8M RA | 14 | 20 |
| 10-8M RA+25uM E3330 | 15 | 31 |
| 10-9M RA | 7 | 10 |
| 10-9M RA+25uM E3330 | 11 | 27 |

Fig. 26

BENZOQUINONE DERIVATIVE E3330 IN COMBINATION WITH CHEMOTHERAPEUTIC AGENTS FOR THE TREATMENT OF CANCER AND ANGIOGENESIS

CROSS REFERENCE TO RELATED APPLICATIONS

This is a Continuation Application of U.S. patent application Ser. No. 12/679,824 (now issued as U.S. Pat. No. 9,040,505) filed on Jul. 6, 2010, which is a U.S. national counterpart application of international application serial No. PCT/US2008/077210 filed on Sep. 22, 2008, which claims priority to U.S. Provisional Patent Application No. 60/975,396 filed on Sep. 26, 2007 and to U.S. Provisional Patent Application No. 60/989,566 filed on Nov. 21, 2007, each of which is incorporated by reference herein in its entirety.

FIELD OF THE INVENTION

The present invention relates generally to the fields of molecular biology, biochemistry, and pathology. More specifically, in certain aspects, the invention relates to the use of Ape1/Ref-1 redox inhibitors in the treatment of cancer and for inhibition of angiogenesis.

BACKGROUND OF THE INVENTION

Apurinic/apyrimidic endonuclease (Ape 1), also known as redox effector factor (Ref-1) (hereinafter Ape1/Ref-1) is an enzyme with a dual role. In addition to its DNA base excision repair (BER) activity, Ape1/Ref-1 also functions as a redox effector maintaining transcription factors in an active reduced state (see FIG. 1).

Ape1/Ref-1 has been shown to stimulate the DNA binding activity of several transcription factors such as HIF-1α, NFκβ, AP-1 and p53, and others known and unknown, which are related to tumor survival and progression (Evans et al., *Mutat Res* 2000, 461, 83). Ape1/ref-1 expression has been shown to be altered in a variety of cancers including breast, cervical, germ cell tumors, adult and pediatric gliomas, osteosarcomas, rhabdomyosarcomas, non-small cell lung cancer, and multiple myeloma (Puglisi et al., *Oncol Rep* 2002, 9, 11; Thomson et al., *Am J Pediatr Hematol Oncol* 2001, 23, 234; Roberston et al., *Cancer Res* 2001, 61, 2220; Puglisi et al., *Anticancer Res* 2001, 21, 4041; Koukourakis et al., *Int J Radiat Oncol Biol Phys* 2001, 50, 27; Kakolyris et al., *Br J Cancer* 1998, 77, 1169; Bobola et al., *Clin Cancer Res* 2001, 7, 3510). High Ape1/Ref-1 expression has also been associated with a poor outcome for chemoradiotherapy, poor complete response rate, shorter local relapse-free interval, poorer survival, and high angiogenesis (Koukourakis et al., *Int J Radiat Oncol Biol Phys* 2001, 50, 27; Kakolyris et al., *Br J Cancer* 1998, 77, 1169; Bobola et al., *Clin Cancer Res* 2001, 7, 3510).

Angiogenesis is an important component of cancer growth, survival, migration, and metastasis. The formation of new blood vessels at the site of a cancerous tumor provides a source of nutrients for accelerated tumor growth and expansion as well as a path for tumor cells to enter the bloodstream and spread to other parts of the body. Thus, effective inhibition of angiogenesis is a useful mechanism to slow or prevent the growth and spread of cancer. An increase in Ape1/Ref-1 activity has been associated with angiogenesis. Vascular endothelial growth factor (VEGF) is an important signaling protein involved in both vasculogenesis and angiogenesis. Ape1/Ref-1 is a component of the hypoxia-inducible transcriptional complex formed on the vascular endothelial growth factor (VEGF) gene's hypoxic response element (Ziel et al., *Faseb J* 2004, 18, 986).

In addition to cancer, altered angiogenesis contributes to pathological conditions related to, among others, cardiovascular disease, chronic inflammatory disease, rheumatoid arthritis, diabetic retinopathy, degenerative maculopathy, retrolental fibroplasias, idiopathic pulmonary fibrosis, acute adult respiratory distress syndrome, asthma, endometriosis, psoriasis, keloids, and systemic sclerosis. Inhibition of angiogenesis is a desirable clinical outcome for the amelioration or prevention of diseases involving excessive angiogenesis.

SUMMARY OF THE INVENTION

Targeted inhibition of the redox function of Ape1/Ref-1 is a novel approach to the treatment of cancer and angiogenesis. In one embodiment, the present invention is directed to the use of anticancer therapeutic agents that inhibit the redox function of Ape1/Ref-1. In another embodiment, the present invention is directed to anti-angiogenic agents that inhibit the redox function of Ape1/Ref-1.

BRIEF DESCRIPTION OF THE DRAWINGS

FIGS. 3A & 3B. VEGF ELISA Assay.

FIGS. 4A & 4B. VEGF ELISA Assay.

FIG. 10. MTS Proliferation Assay with retinal endothelial cell proliferation in cells treated with or without basic fibroblast growth factor (bFGF).

FIG. 20. Survival data of mice treated with RN3-3 (E3330) at various amounts and observed on days 2, 3, 4 or 5 after treatment.

FIGS. 21A & 21B. Pharmacokinetic data of E3330 (RN3-3) over a 24 hr time course experiment.

FIG. 22. Pharmacokinetic data for E3330 (RN3-3).

FIG. 25. Effect of RN3-3 (E3330) and various doses of RA.

FIG. 26. Effect of E3330 (RN3-3) and RA on HL-60 cells undergoing apoptosis (annexin/PI assay).

DETAILED DESCRIPTION

Figure 1:
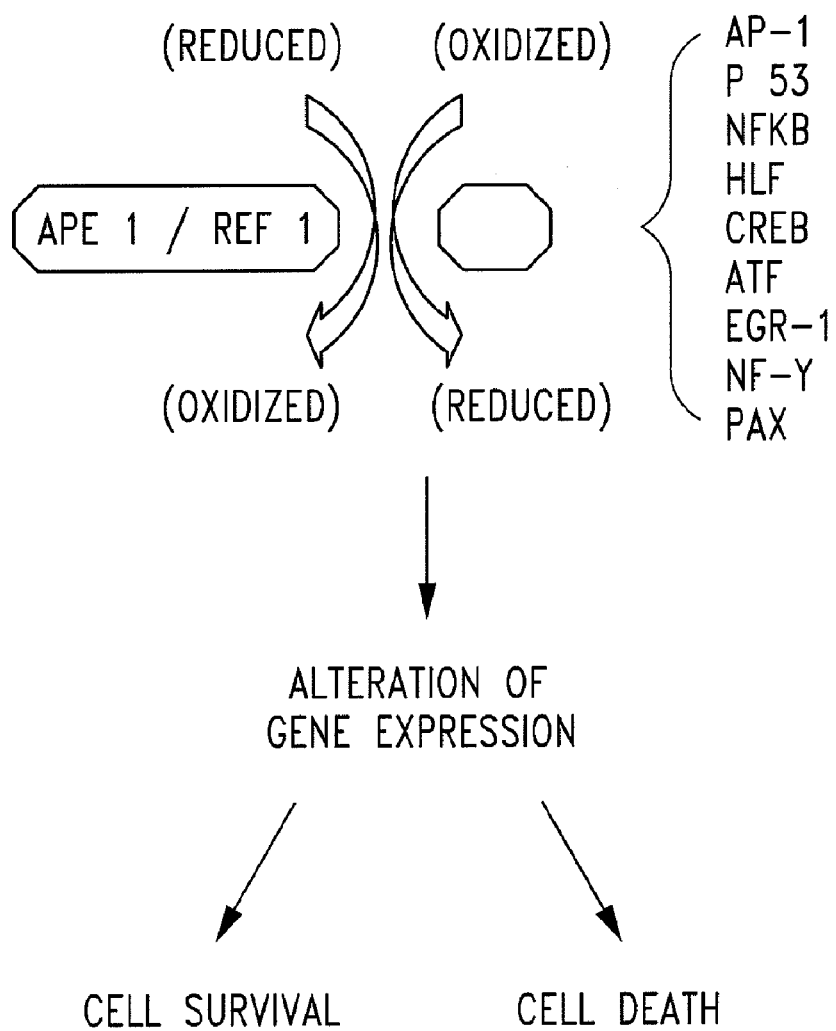
FIG. 1. Redox role of Ape1/Ref-1 in the regulation of transcription factors important in tumor survival.

The present invention is directed to the use of anti-cancer and anti-angiogenic agents that selectively inhibit the redox function of Ape1/Ref-1. Such selective inhibition includes specific inhibition, or, in other words, where there is no or no appreciable effect on the BER function of APE1/Ref-1, as well as where the predominant effect is on the redox function, vis-a-vis the BER function. Also encompassed by the invention is the use of such agents in combination with additional chemotherapeutic/therapeutic agents. It is desired that the other agents work on a subject in a different way to that of the agents which selectively inhibit the redox function of Ape1/Ref1.

Physiological disorders associated with altered angiogenesis encompass those disorders associated with inappropriate angiogenesis, which are directly or indirectly deleterious to the subject. Altered angiogenesis contributes to pathological conditions related to, among others, cancer (including growth, survival, migration, microenvironment, and metastasis), and cardiovascular disease, chronic inflammatory disease, rheumatoid arthritis, diabetic retinopathy, degenerative maculopathy, retrolental fibroplasias, idiopathic pulmonary fibrosis, acute adult respiratory distress syndrome, asthma, endometriosis, psoriasis, keloids, and systemic sclerosis.

The term subject includes vertebrate animals, and preferably is a human subject. The term inhibit, and derivates thereof, includes its generally accepted meaning, which includes prohibiting, preventing, restraining, and slowing, stopping, or reversing progression or severity. Thus, the present methods include both medical therapeutic and prophylactic administration, as appropriate. As such, a subject in need thereof, as it relates to the therapeutic uses herein, is one identified to require or desire medical intervention. An effective amount is that amount of an agent necessary to inhibit the pathological diseases and disorders herein described. When at least one additional therapeutic agent is administered to a subject, such agents may be administered sequentially, con-currently, or simultaneously, in order to obtain the benefits of the agents.

The redox function of Ape1/Ref-1 was found to be selectively inhibited by 3-[(5-(2,3-dimethoxy-6-methyl1,4-benzoquinoyl)]-2-nonyl-2-proprionic acid, below (hereinafter "E3330", also referred to as "RN3-3" in this application). Further information on E3330 may be found in Abe et al., U.S. Pat. No. 5,210,239, fully incorporated herein by reference. Particularly, processes for preparing, formulations, and pharmaceutically acceptable salts are described.

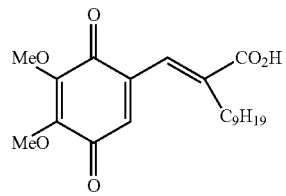

Interestingly, our research indicates that selective blocking of the redox function of Ape1/Ref-1 does not cause any or any appreciable apoptosis in normal cells. One very well might expect that the selective blocking resulting in increased apoptosis in cancerous cells would also impair normal cells. However, we have not found this to be the case.

Where subject applications are contemplated, particularly in humans, it will be necessary to prepare pharmaceutical compositions in a form appropriate for the intended application. Generally, this will entail preparing compositions that are essentially free of impurities that could be harmful to a subject.

The agents can be administered orally, intravenously, intramuscularly, intrapleurally or intraperitoneally at doses based on the body weight and degree of disease progression of the subject, and may be given in one, two or even four daily administrations.

One will generally desire to employ appropriate salts and buffers to render agents stable and allow for uptake by target cells. Aqueous compositions of the present invention comprise an effective amount of the agent, dissolved or dispersed in a pharmaceutically acceptable carrier or aqueous medium. Such compositions also are referred to as innocuously. The phrase pharmaceutically or pharmacologically acceptable refers to molecular entities and compositions that do not produce adverse, allergic, or other untoward reactions when administered to a subject. As used herein, pharmaceutically acceptable carrier includes any and all solvents, dispersion media, coatings, antibacterial and antifungal agents, isotonic and absorption delaying agents and the like. The use of such media and agents for pharmaceutically active sub-stances is well known in the art. Supplementary active ingre-dients also can be incorporated into the compositions.

Compositions for use in the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically accept-able compositions, described supra.

For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium com-pounds; surface active agents such as cetyl alcohol, glycerol monosteatrate; adsorptive carriers such as kaolin and bentonite; and lubricants such as talc, calcium and magnesium stearate, and solid polyethyl glycols.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration agents of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including gels, pastes, powders and slurries. The active ingredient may be added in a therapeutically effective amount to a paste dentifrice that may include water, binders, abrasives, flavoring agents, foaming agents, and humectants.

The compositions for use in the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, general safety and purity standards as required by FDA and foreign counterpart agencies.

Inhibition of the redox function of Ape1/Ref-1 was shown to decrease VEGF release, impair capillary tube formation, and inhibit the growth of large cell number colonies, indicating anti-angiogenic activity. The following examples are for illustrative purposes only and are not intended to limit the scope of the present invention.

Figure 2:
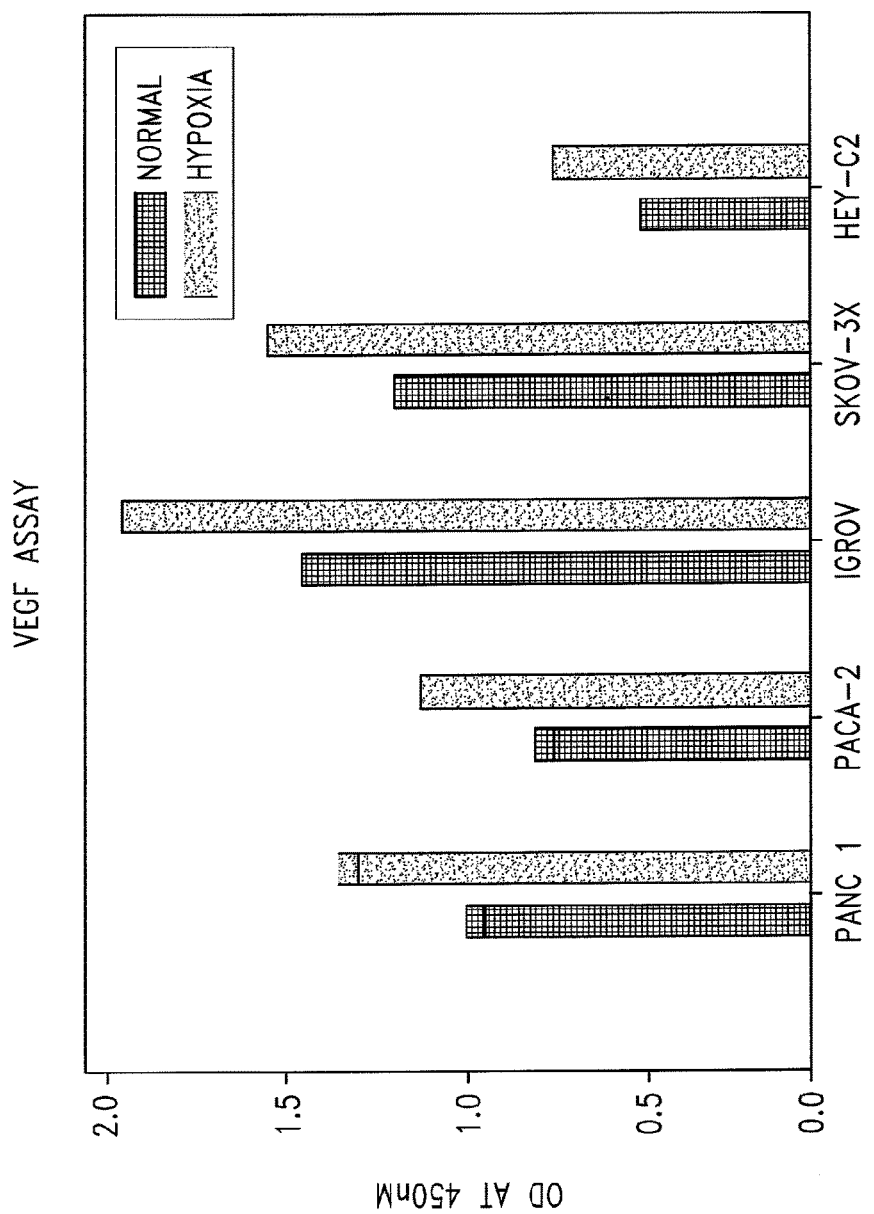
FIG. 2. VEGF enzyme-linked immunosorbent assay (ELISA).
Figure 5:
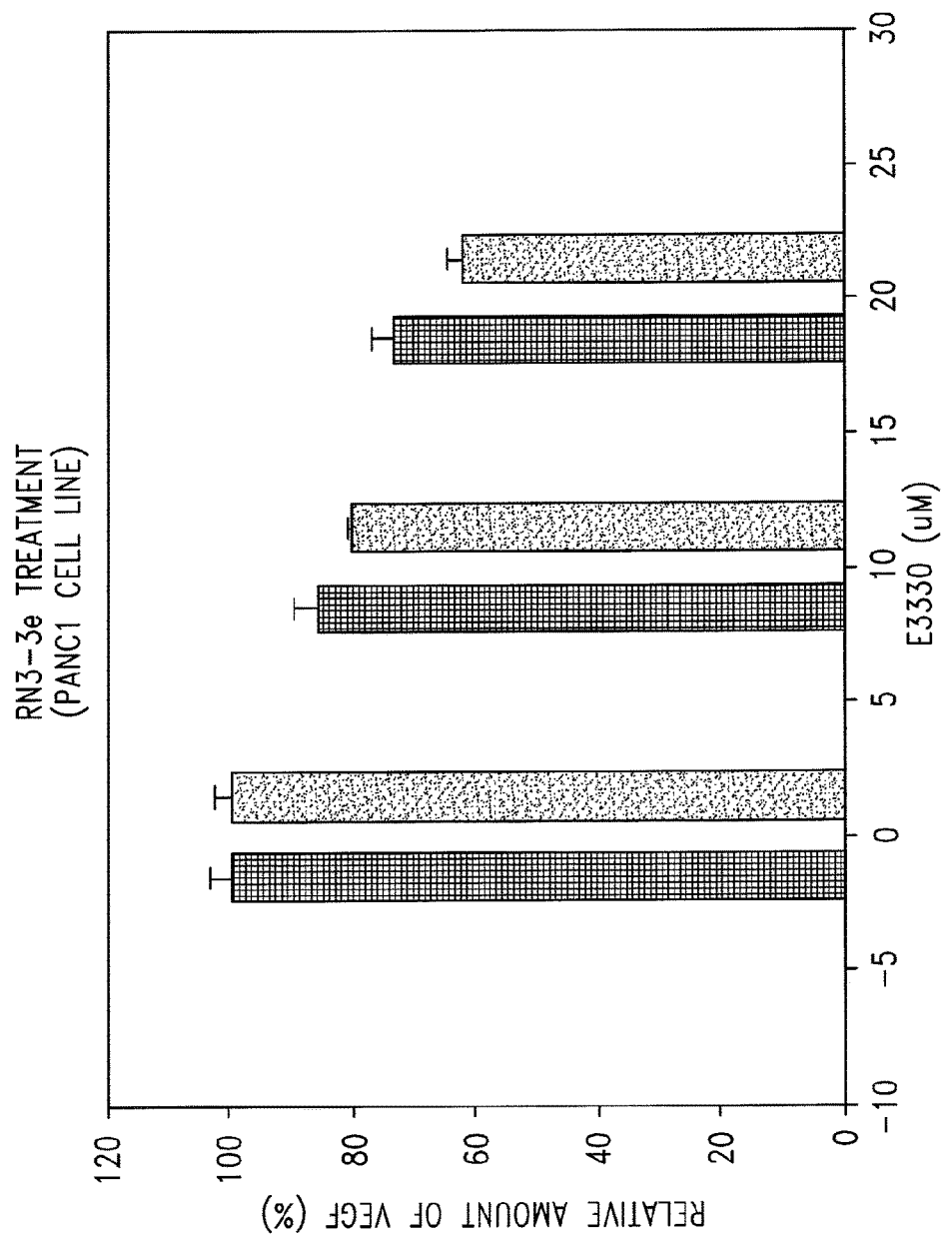
FIG. 5. VEGF ELISA Assay.
Figure 6:
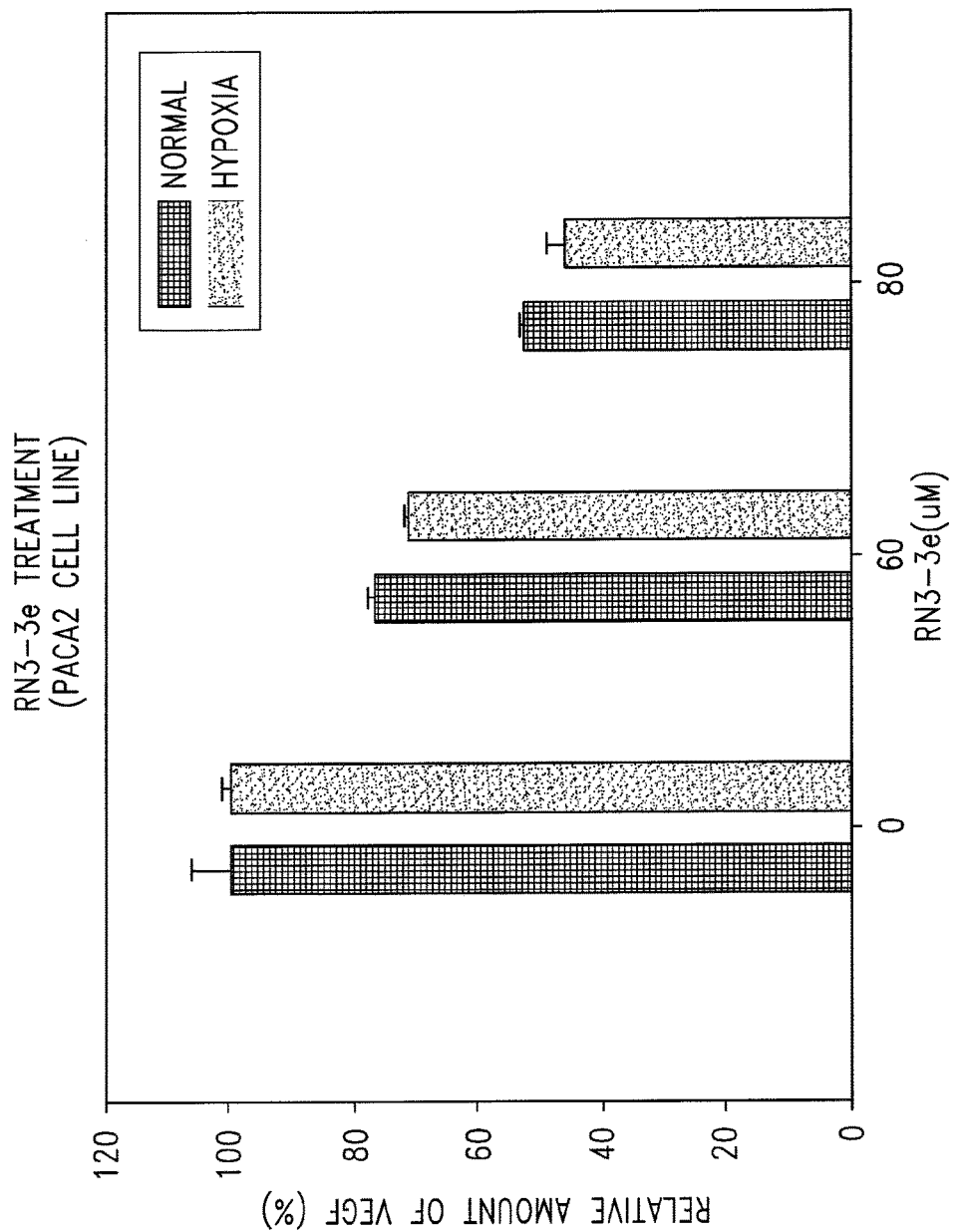
FIG. 6. VEGF ELISA Assay.
Figure 7:
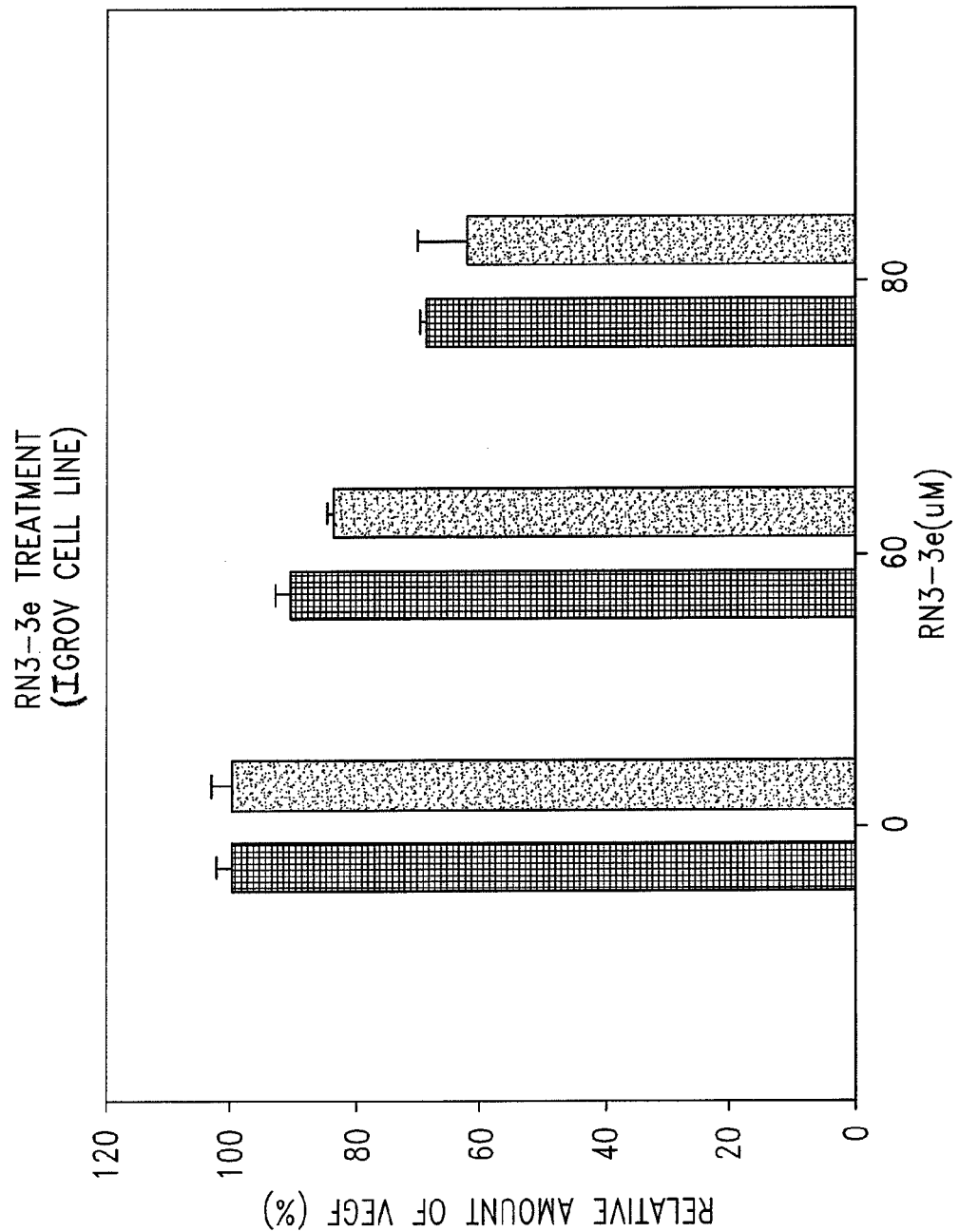
FIG. 7. VEGF ELISA Assay.

Inhibition of VEGF release. VEGF enzyme-linked immunosorbent assay (ELISA). Various cancer cell lines were plated in a 24-well plate and treated in duplicates with for about 24 hrs in normoxic (about 21% oxygen) or hypoxic (about 2% oxygen) condition. The supernatants of cells were collected and subjected to an ELISA assay with a kit specific for human VEGF according to the manufacturer (R&D Sys-tems, Minneapolis, Minn.) VEGF ELISA assay results were read in a 96-well format plate reader by measuring absor-bance at 450 nm with correction at 540 nm. Hypoxia induced an increase in VEGF release (FIG. 2). (For FIGS. 2-7, black bars=normoxia; gray bars=hypoxia.)

VEGF ELISA Assays. Hey-C2 (ovarian cancer), SKOV-3X (ovarian cancer), Panc1 (pancreatic cancer), PaCa-2 (pancreatic cancer), and Igrov (ovarian cancer) cells were plated in a 24-well plate and treated in duplicates with E3330 (RN3-3 e) at different concentrations for about 24 hrs in normoxic (about 21% oxygen) or hypoxic (about 2% oxygen) condition. The supernatants of cells were collected and subjected to an ELISA assay with a kit specific for human VEGF according to the manufacturer (R&D Sys-tems, Minneapolis, Minn.). VEGF ELISA assay results were read in a 96-well format plate reader by measuring absor-bance at 450 nm with correction at 540 nm. E3330 (RN3-3e) reduced the amount of VEGF release from the cells under both normoxia and hypoxia conditions through inhibition of Ape 1/Ref-1 redox function (FIGS. 2-7).

Inhibition of capillary tube formation. The capillary tube formation assay was performed using CB-ECFC cells plated on Matrigel and treated with E3330 or control media. ECFCs were cultured as previously described (Blood, 1 Nov. 2004, Vol. 104, No. 9, pp. 2752-2760). ECFC colonies appeared between 5 and 22 days of culture. Colonies were counted by visual inspection using an inverted microscope (Olympus, Lake Success, N.Y.) under ×40 magnification. Cells were passaged as previously described. Blood, 1 Nov. 2004, Vol. 104, No. 9, pp. 2752-2760.)

Figure 8:
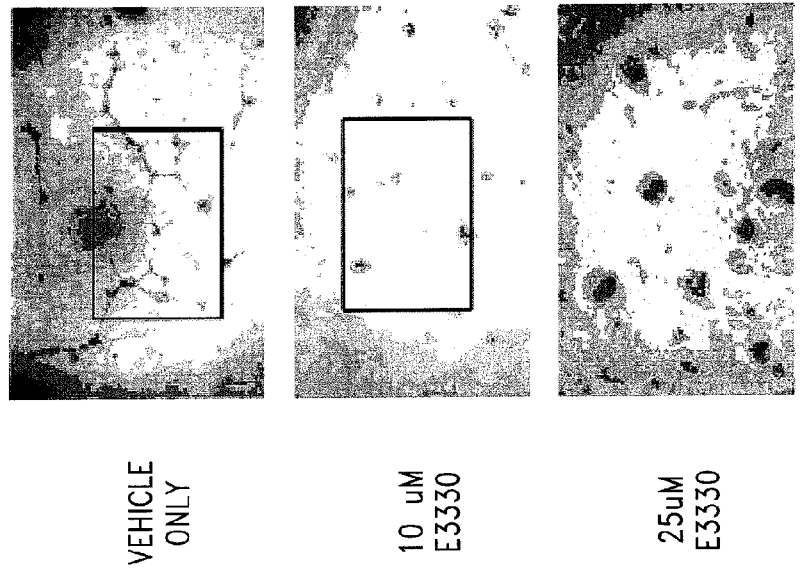
FIG. 8. Capillary tube formation assay using CB-ECFC cells plated on Matrigel.

The tube formation assay was performed as described previously (J. Biol. Chem. 274 (1999), pp. 35562-135570). Various concentrations of E3330 were given to CB-ECFCs for about 30 min at room temperature before seeding and plated onto the layer of matrigel at a density of about $1 \times 10^4$ cells/well. After about eight hours, the enclosed networks of complete tubes from randomly chosen fields were counted and photographed under a microscope. E3330 and its analogues inhibit tube formation, an indicator of anti-angiogenesis and growth inhibition (FIG. 8).

Figure 9:
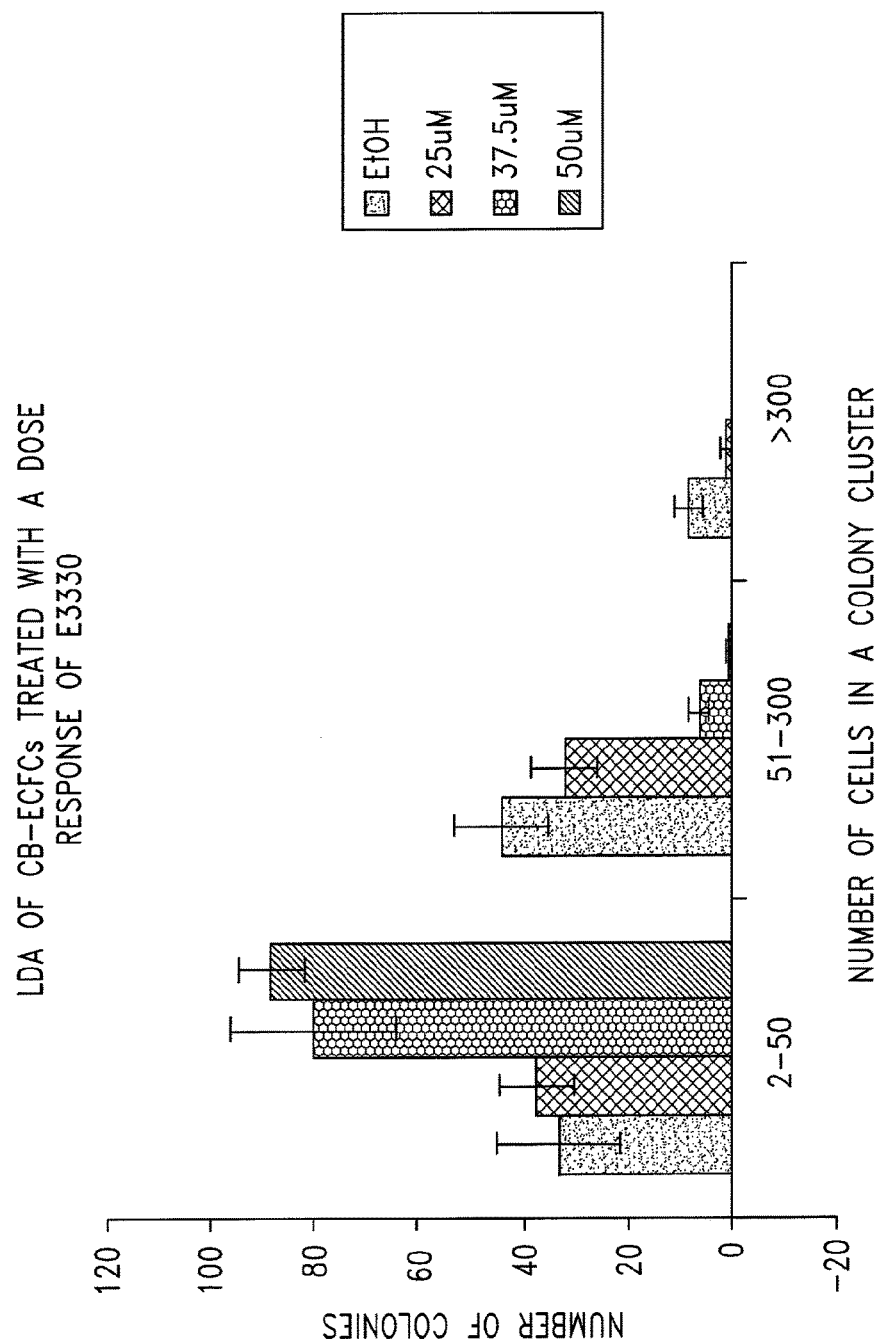
FIG. 9. Limiting dilution assay (LDA).

Limiting dilution assay. E3330 inhibit growth of large cell number colonies in the limiting dilution assay (LDA) which is also an indicator of anti-angiogenesis (FIG. 9). ECFCs were cultured as previously described (Blood, 1 Nov. 2004, Vol. 104, No. 9, pp. 2752-2760). ECFC colonies appeared between 5 and 22 days of culture. Colonies and the number of cells per colony were counted by visual inspection using an inverted microscope. E3330 inhibit growth of large cell number colonies in the limiting dilution assay (LDA) which is also an indicator of anti-angiogenesis. Increasing amounts of E3330 (RN3-3) leads to a decrease in the number of colonies with large numbers of cells and an increase in colonies with only small cell numbers indicative of inhibition of cell growth. (FIG. 9). (In FIG. 9, the bars are, left to right, EtOH, and E330 dosed at 25 µM, 37.5 µM, and 50 µM.)

Figure 11:
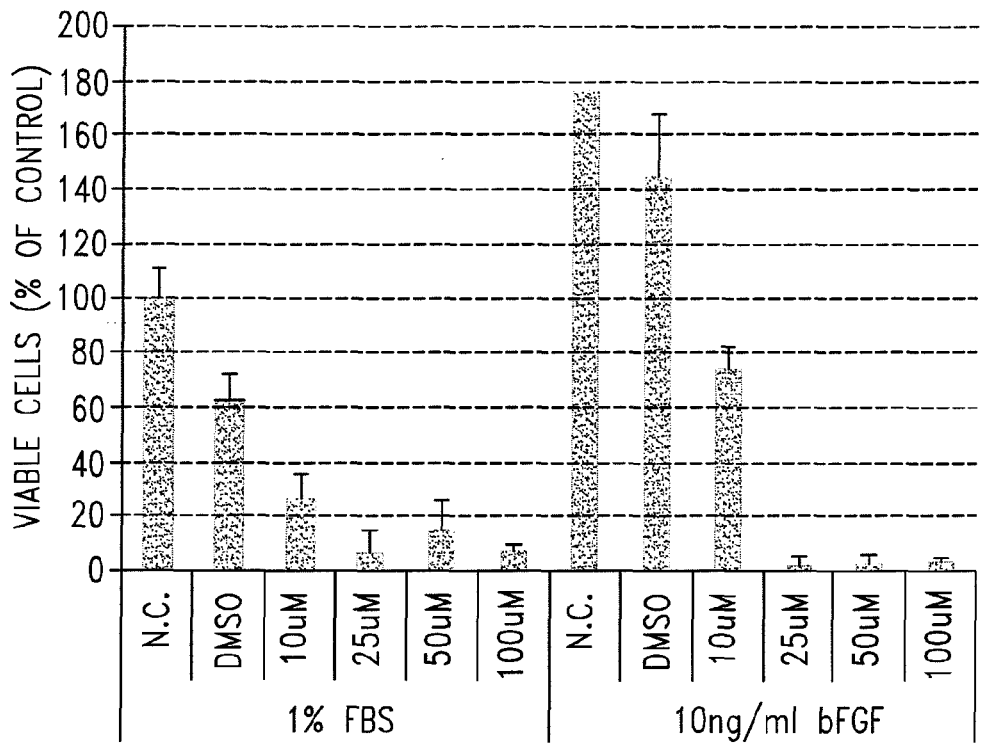
FIG. 11. Effect of E3330 (RN3-3) on the proliferation of retinal vascular endothelial cells (RVEC)-wild/sv40 cells.

Inhibition of endothelial cell proliferation. E3330 at about 10-100 µM decreased retinal endothelial cell proliferation in cells treated with or without basic fibroblast growth factor (bFGF). Young adult mouse retinal tissues were dissected out and digested. Cells were plated in 24 well plates and grown to confluence, then seeded to 96 well plates for assay. Three days after seeding, the total number of cells was assayed by MTS measurement (Promega). The proliferation rate was calculated according to manufacturer's instructions. Proliferations of RECs from different groups were compared for statistical significance. E3330 (RN3-3) blocked REC proliferation indicative of anti-blood vessel formation effects. (FIG. 10) E3330 10-100 µM decreased cell proliferation of retinal vascular endothelial cells (RVEC) (FIG. 11). In basal media, E3330 inhibited REVC cell proliferation at all 4 concentrations tested, 10 µM-57%, 25 µM-93% ($p<0.01$). REC proliferation was significantly boosted when bFGF was added in the media. A similar inhibitory effect was also seen in bFGF media at 10 µM, 25 µM, and higher concentration of E3330.

In vitro tube formation assay. Additionally, it was observed that in an assay observing in vitro tube formation, E3330, like Avastin, prevented formation of blood-vessel-like tubules in endothelial cells, in a dose dependent manner. In that assay it was also observed that a combination use of Avastin and E3330 was synergistically more effective than either alone.

SNV in vldlr-/- knockout mice assay. It has been observed E3330 intravitreal treatment significantly reduces the number of subretinal neovascularization (SNV) in vldlr-/- retina. Experiments were carried out in very-low-density lipoprotein receptor (vldr) knockout mice to determine the effect of E3330 on inhibition of SNV development in the vldlr-/- mutant. Each animal received a single intravitreal injection of 1 µl volume of BSS as a vehicle control and the fellow eye received 1 µl of 200 nm E3330. The final concentration of E3330 was equivalent to approximately 20 µM in the retina. Quantitative measurement of SNV was carried out one week after the treatment in the whole mount retina after lectin-FITC staining. The results showed that 17/20 individuals had reduced number of SNV in the eyes treated with E3330 with ~30% reduction. In contrast, neither Avastin (VEGF antibody) nor bFGF antibody treatment showed any sign of inhibition to the number of SNV. The apparent increase of SNV after antibody injection could be due to foreign protein triggered immune response which has been reported before (Tator et al., 2008). E3330 reduced the number of SNV at a statistically significant level ($p<0.01$ in paired t-test). These data are very encouraging as this model of retinal angiomatous proliferation (RAP), similar to human, is difficult to treat and does not respond well to current avail-able treatments including anti-VEGF and anti-bFGF agents. The Ape1/Ref-1 inhibitor offers a new approach to control angiogenesis for advanced macular degeneration (AMD) treatment.

The present invention also encompasses the use of agents that inhibit the redox function of Ape 1/Ref-1 as anti-cancer therapeutics. Such cancers include breast, prostate, pancreatic, colon, cervical, germ cell tumors, adult and pediatric gliomas, osteosarcomas, rhabdomyosarcomas, non-small cell lung cancer, leukemias, and multiple myeloma. Ape1/Ref-1 has been shown to stimulate the DNA binding activity of several transcription factors such as HIF-1α, NFκβ, AP-1 and p53, which are related to tumor survival and progression. Selective inhibition of the redox function of Ape1/Ref-1 by E3330 decreases the binding of transcription factors to DNA and impairs the ability of cancer cells to thrive. The following examples are for illustrative purposes only and are not intended to limit the scope of the present invention.

Figure 12:
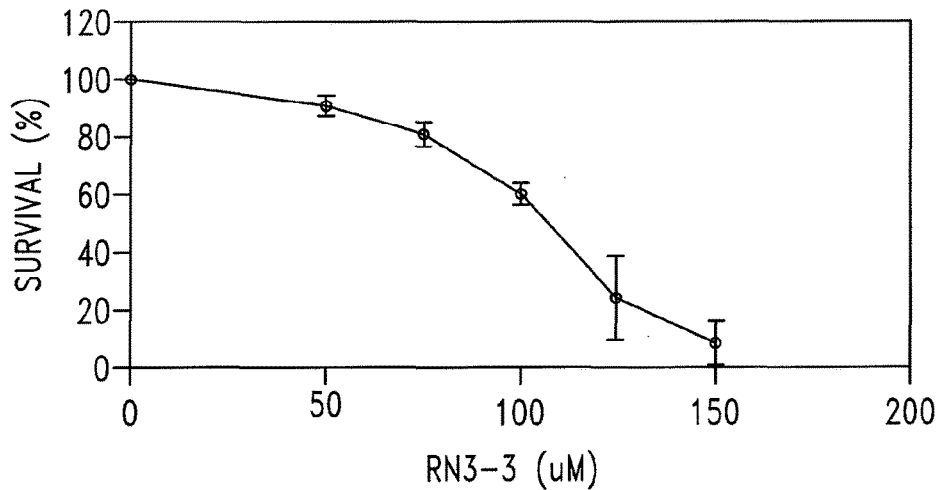
FIG. 12. MTS assay using MCF-7 tumor cells derived from human breast adenocarcinoma. 3-(4-5-Dimeth-ylthi-azol-2-yl)-5-(3-carboxymethoxyphenyl)-2-(4-sulfophe-nyl)-2H-tetrazolium salt (MTS) assay used for cell survival/growth analysis.
Figure 13:
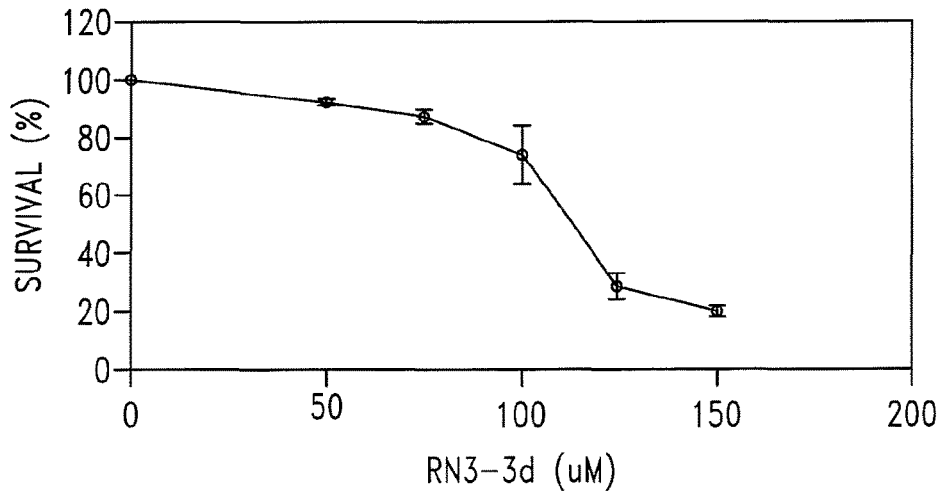
FIG. 13. MTS assay using OVCAR-3 tumor cells derived from human ovarian adenocarcinoma.
Figure 14A:
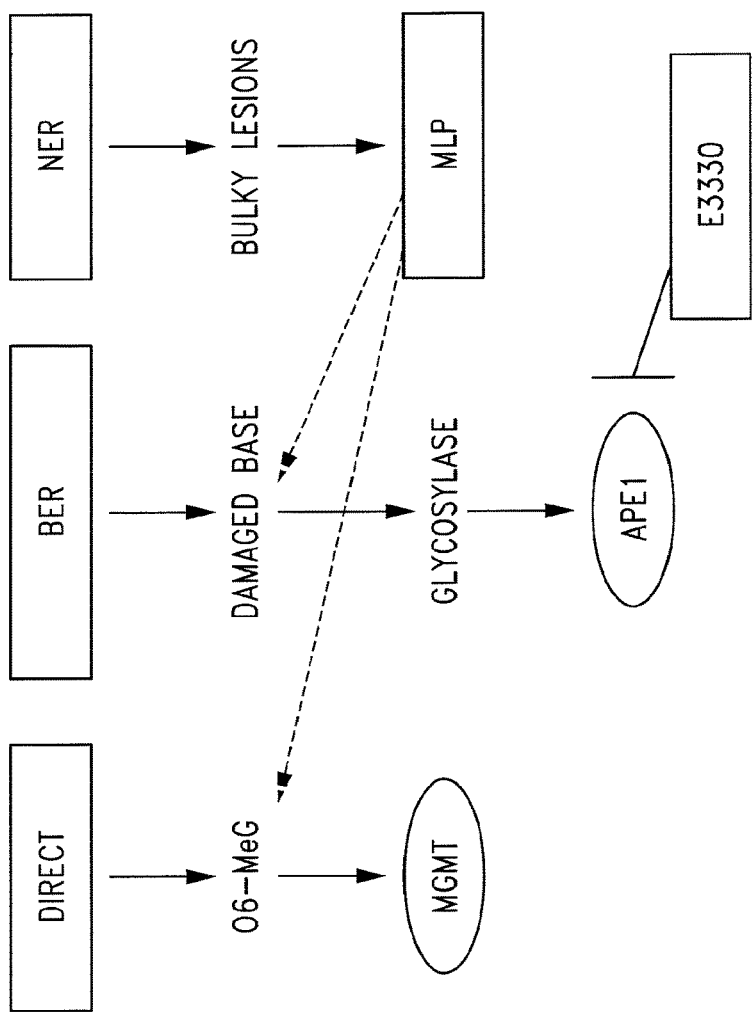
FIGS. 14A-14D. Effect of E3330 (RN3-3) in combination with the chemotherapeutic drug melphalan on multiple myeloma cells.
Figure 14B:
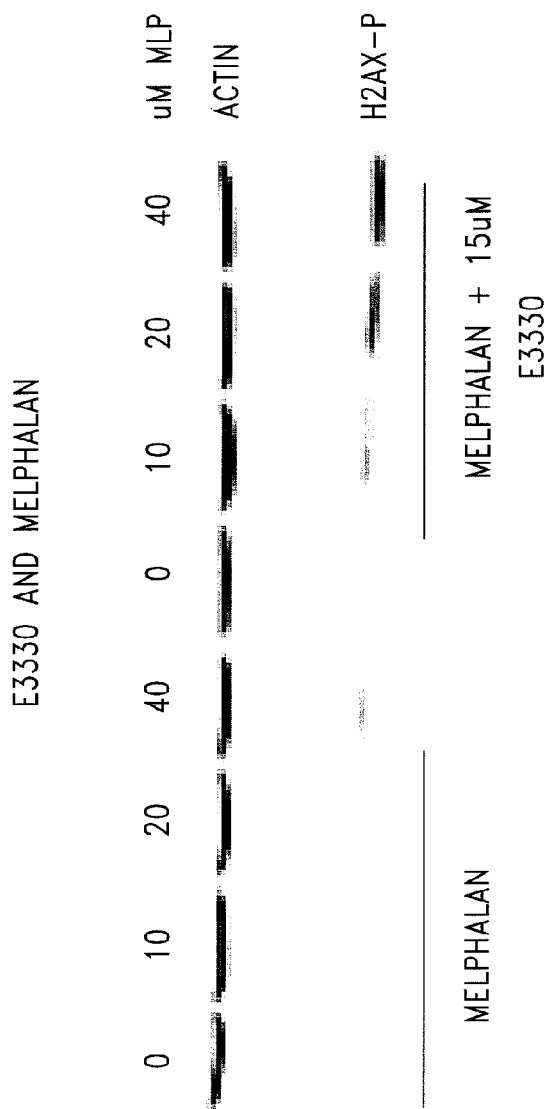
Figure 14C:
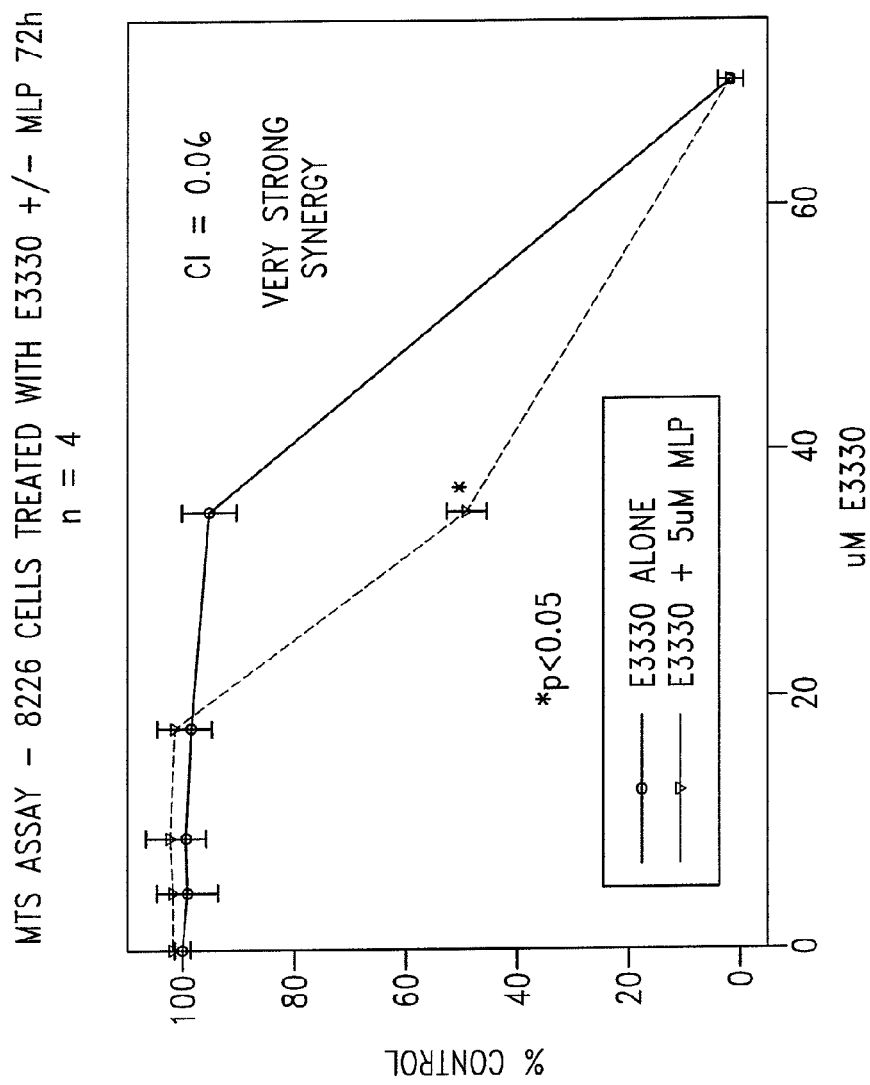
Figure 14D:
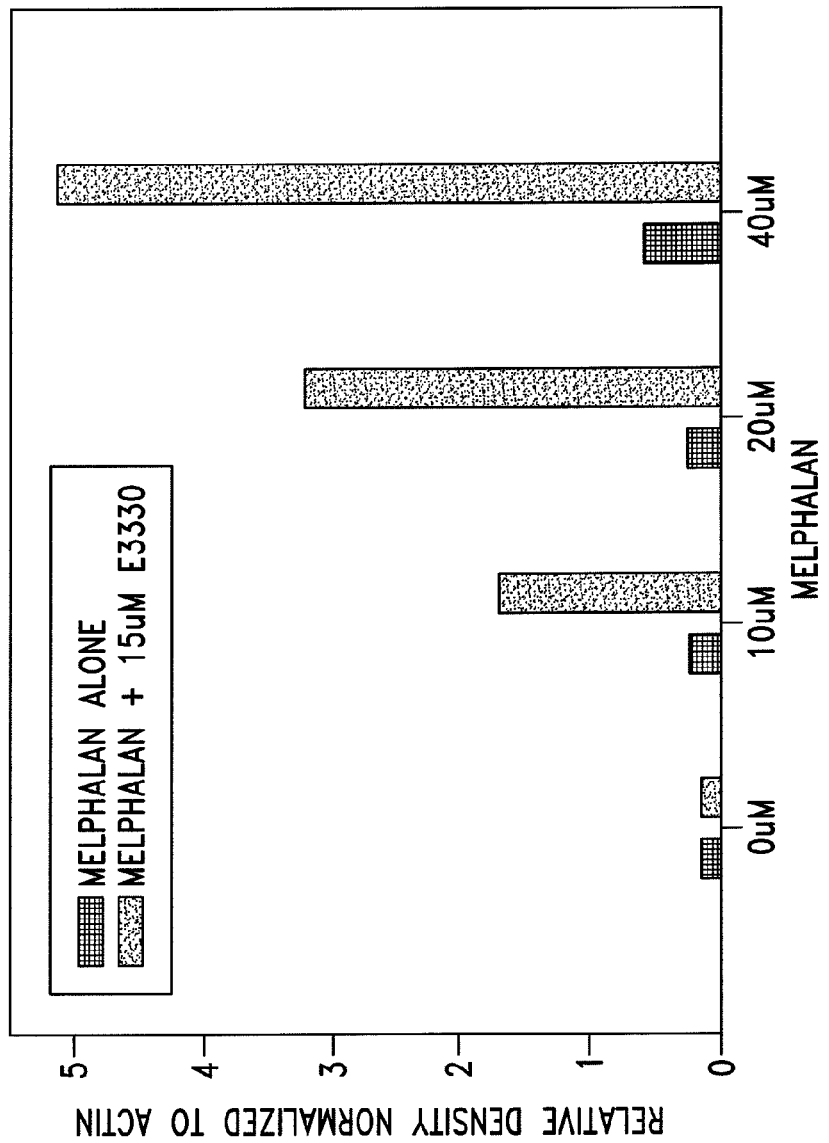

Decreased cancer cell survival. MCF-7 or OVCAR-3 cells (about 2-4,000) were aliquoted into each well of a 96-well plate in triplicate and allowed to adhere overnight. E3330 (RN3-3) was added to the cultures. After about or 72 h, about 0.05 mg/mL 3-(4-5-Dimethylthiazol-2-yl)-5-(3-carboxymethoxyphenyl)-2-(4-sulfophenyl)-2H-tetrazolium salt (MTS) reagent was added to each well and incubated at about 37° C. for about 4 h followed by absorbance measurement at 490 nm. The values were standardized to wells containing media alone. Independently, E3330 dose dependently killed MCF-7 tumor cells derived from human breast adenocarcinoma (FIG. 12) and OVCAR-3 tumor cells derived from human ovarian adenocarcinoma (FIG. 13). Similar effects can be seen in multiple myeloma, prostate, non-small cell lung carcinoma, colon, and glioma derived cells. In contrast, significant growth inhibition in our studies with normal cells such as hematopoietic embryonic cells or in human CD34+ progenitor cells was not observed. These data are novel in that they implicate the redox role of Ape1/REF-1 in cancer, but not "normal" cell survival.

Glioma Cell Migration Assay. E3330 was tested to determine if it would inhibit the migration ability of SF767 glioma cells. In order to do this, we plated 1.5×106 SF767 cells in a 60 mm tissue culture dish and allowed them to attach overnight and form a confluent monolayer. A scratch or wound was made across the plate using a 200 [IL pipette tip as described previously (Liang 2007). The cells were then rinsed to remove floating cells and media contain 25, 50, 75 or 100 E3330 or the appropriate vehicle control, DMSO. The drug-containing media was removed after 24 h and fresh media was added. Images were taken at three marked places along the scratch at 0, 24, 36 and 48 h after the drug was added. Migration was quantified in ten uniform places for each image taken using Spot Software (Diagnostic Instruments, Sterling Heights, Mich.) to measure the distance in microns between the leading edges of the scratch. Each set of data, a total of thirty for each data point, was normalized to the migration of the vehicle control at 0 h and used to determine standard deviation. The results indicate the E3330 inhibited the ability of the SF767 cells to migrate, and exhibited as much as 4.0-fold inhibition with 100 µM E3330-treated cells as compared to the vehicle control at 48 h.

Our results support an effect on the microenvironment, or stroma. The microenvironment, which is distinct from the cancer cells per se, plays a part in a tumor's progression, including metastasis. It can limit the access of therapeutics to the tumor, alter drug metabolism, and contribute to drug resistance. Clearly, being able to affect the microenvironment can assist in the ultimate therapeutic results achieved in regard to tumors.

In another embodiment, the present invention is directed to the use of agents that inhibit the redox function of Ape1/Ref-1 in combination with other therapeutics. Such therapeutics include, but are not limited to, melphalan, gemcitabine, cisplatin, methoxyamine, thalidomide and its derivatives, and retinoic acid (RA). Selective Ape1/Ref-1 inhibition can act synergistically with other therapeutics to increase anticancer efficacy. Thus, lower doses of therapeutics, which cause sickness and are toxic to normal cells at higher doses, can be administered without a decrease in anti-cancer efficacy. Use of agents that selectively inhibit the redox function of Ape1/Ref-1 can provide protection for normal cells against the effects of cisplatin and other chemotoxic compounds. The following examples are for illustrative purposes only and are not intended to limit the scope of the present invention.

E3330 in combination with chemotherapeutic Melphalan. E3330 in combination with the chemotherapeutic drug melphalan synergistically enhanced killing of multiple myeloma cells (FIGS. 14A-14D). Synergistic plots made using CalcuSyn software. E3330 was either given alone or in combination with melphalan. As an indicator of DNA double stranded breaks (DSBs), the phosphorylation of histone H2AX at Seri' was measured with a phosphorylation-specific H2AX antibody from Upstate Cell Signaling Solutions (Waltham, Md.). Cells were treated with melphalan alone or melphalan plus E3330. After drug treatment, exponentially growing cells were harvested, washed in cold PBS, and lysed in about 100 µL RIPA assay buffer as described above. Protein was quantified and electrophoresed in SDS gel-loading buffer on a 12% SDS-polyacrylamide gel. Mouse monoclonal anti-phosphohistone H2AX (about 1:1000) or anti-actin antibody (about 1:1000; as a loading control, LabVision Corp., NeoMarkers, Fremont, Calif.) was used to probe for protein levels as described previously. Bands were detected using a chemiluminescence kit from Roche Applied Bio-sciences (Indianapolis, Ind.). The bands were visualized using Bio-Rad Chemidoc XRS (Hercules, Calif.) and quantitated using Chemidoc software, Quantity One 4.6.1. There is an increase in DSBs in the melphalan plus E3330 (RN3-3) compared to melphalan alone.

Figure 15:
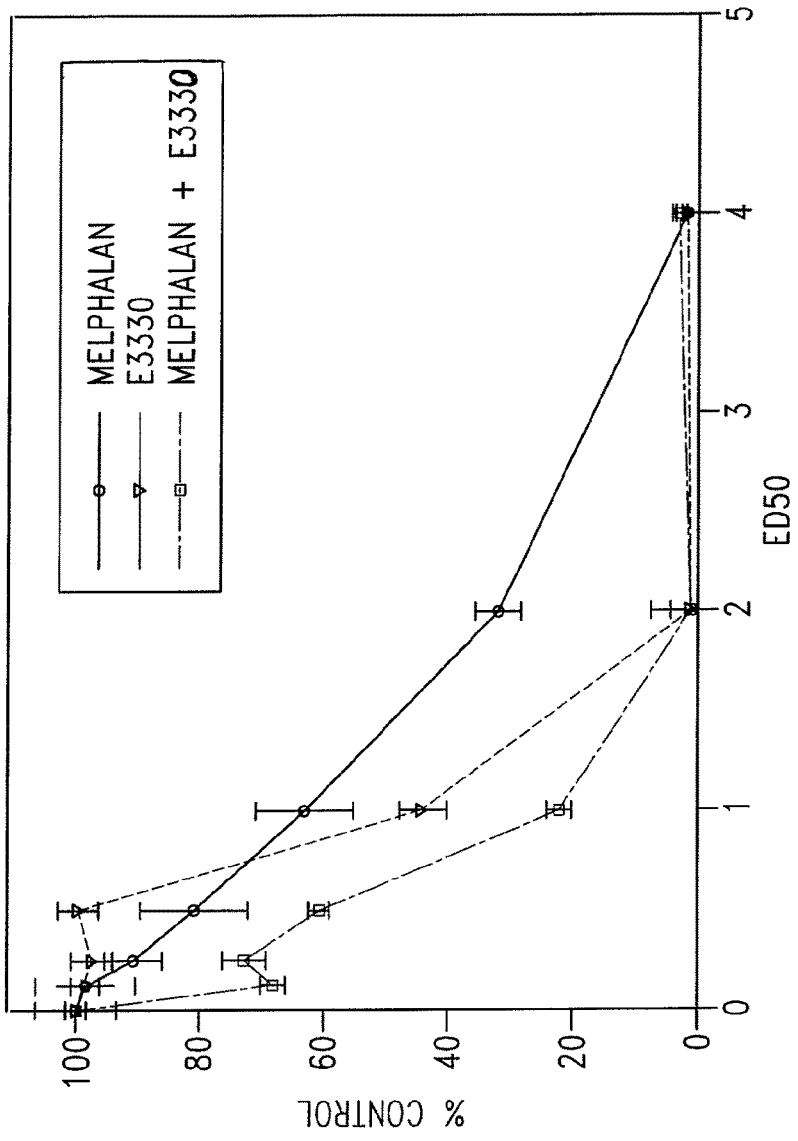
FIG. 15. Effect of E3330 (RN3-3) in combination with chemotherapeutic drug melphalan on multiple myeloma cells in the MTS assay after 72 hours.

E3330 (RN3-3) was applied in combination with the chemotherapeutic drug melphalan and was found to synergistically enhance the killing of multiple myeloma cells in the MTS assay after 72 hours (FIG. 15). E3330 (RN3-3) was either given alone or in combination with melphalan and the ED50 plotted against the percent control as per the CalcuSyn software which is based on the Chou-Talalay algorithm (Chou-Talalay; Advances in Enzyme Regulation 22, 27-55). Melphalan plus E3330 (RN3-3) is more effective than either agent alone.

Figure 16:
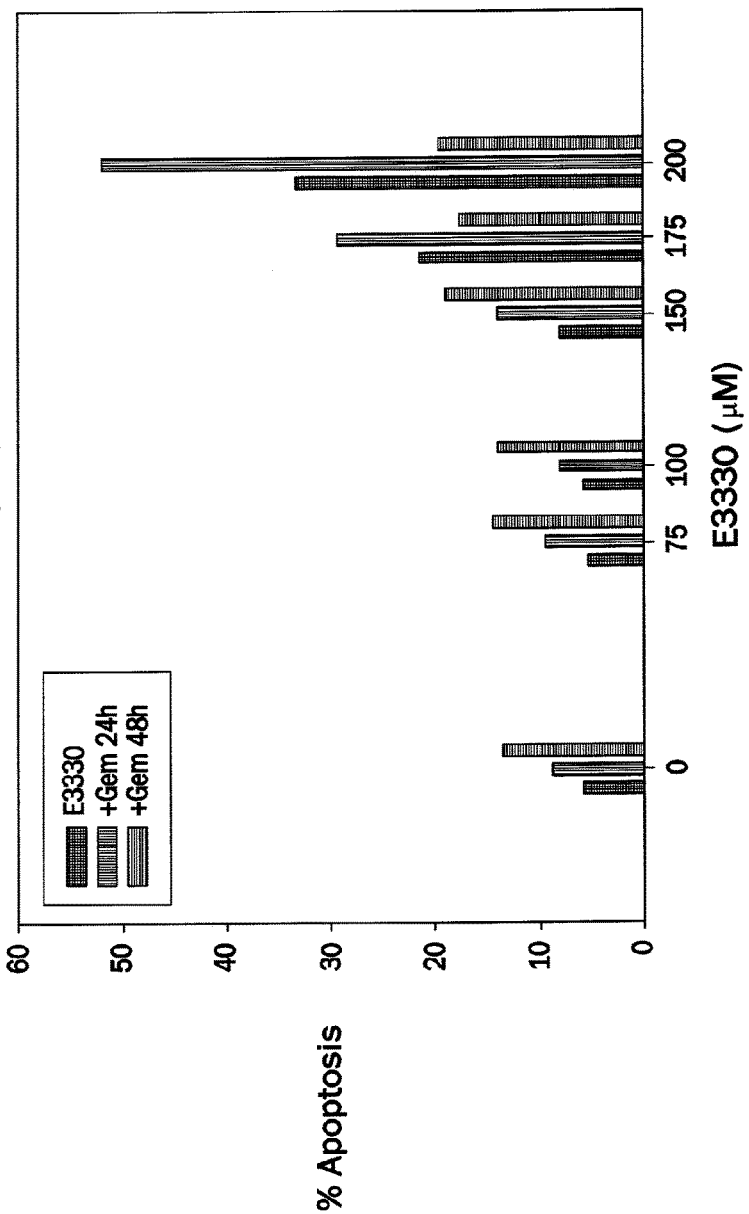
FIG. 16. Effect of E3330 (RN3-3) and gemcitabine (0.25 µM) on pancreatic tumor cells at 24 and 48 hours.

E3330 in combination with chemotherapeutic Gem-citabine. E3330 enhanced the apoptosis inducing effects of gemcitabine (about 0.25 µM) in pancreatic tumor cells (FIG. 16). To analyze the cells for apoptosis, cells were plated and allowed to attach overnight. Cells were treated with E3330 alone or with gemcitabine. Apoptosis was assayed about 24 and 48 hr following treatment. Cells were trypsinized, pelleted, washed in ice-cold PBS, and resuspended in 1× binding buffer [about 10 mmol/L HEPES/NaOH (pH 7.4), 140 mmol/L NaCl, 2.5 mmol/L $CaCl_2$]. Apoptosis was analyzed using the Alexa Fluor 488 AnnexinV from Vybrant Apoptosis Assay kit in combination with propidium iodide (Molecular Probes, Eugene, Oreg.) as described previously Clinical Cancer Research 13, 260-267, Jan. 1, 2007. Cells that were strongly Annexin positive were considered positive for apoptosis. The samples were analyzed by flow cytometry in the Indiana University Cancer Center flow cytometry facility.

Figure 17:
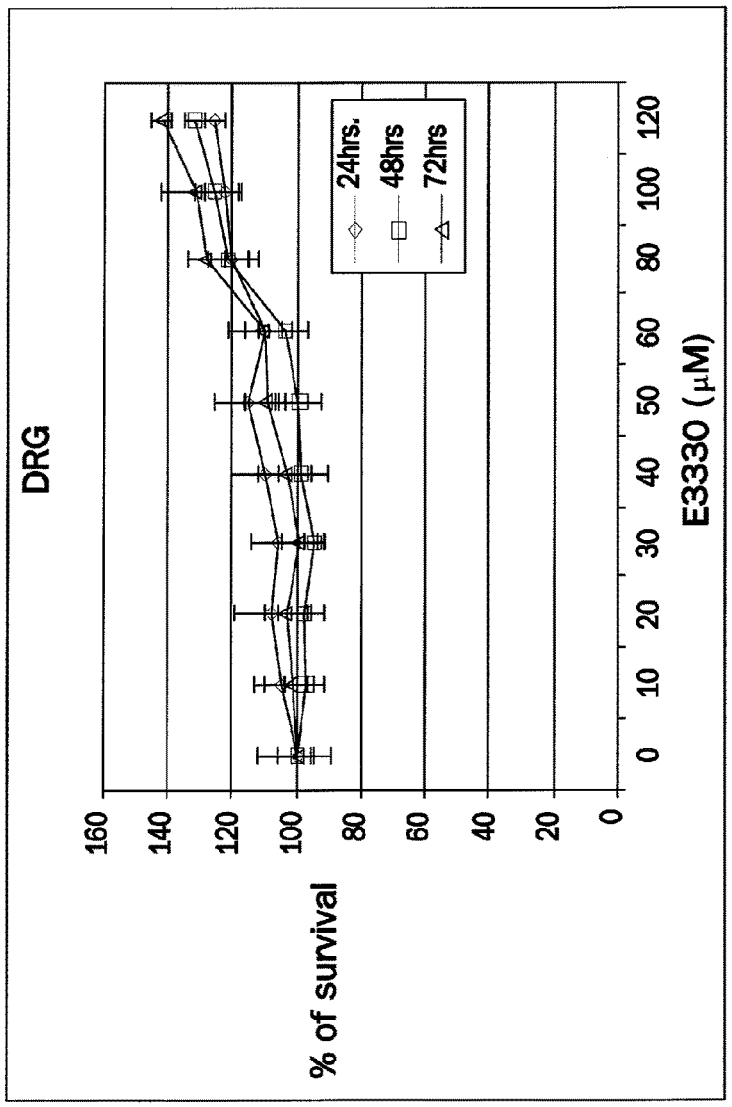
FIG. 17. MTS cell viability assay.

E3330 in combination with chemotherapeutic Cisplatin. Concentrations of E3330 as high as about 1201AM did not impair the survival of rat dorsal root ganglion cells growing in culture for up to about 72 hours, as measured by the MTS cell viability assay (FIG. 17). There was no effect of E3330 (RN3-3) on the post-mitotic DRG cells, indicative of a non-toxic effect of E3330 (RN3-3) on non-dividing cells.

Figure 18:
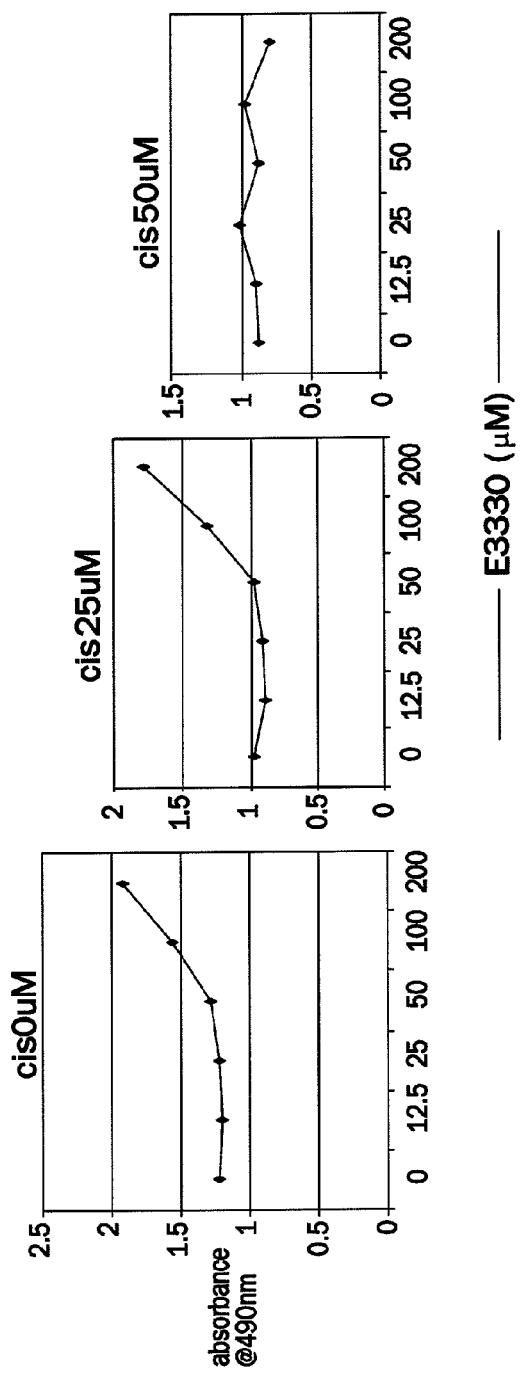
FIG. 18. MTS cell viability assay.

DRG cell cultures and treatments were performed similar to previously published procedures using just E3330 alone (DNA Repair Volume 4, Issue 3, 2 Mar. 2005, pp 367-1379). Further, E3330 provided protection against the neuro-toxic effects of the chemotherapeutic cisplatin when administered to rat dorsal root ganglion cells (FIG. 18). This demonstrates that while E3330 (RN3-3) enhances some chemotherapeutic agents, it has a protective effect on non-dividing, post-mitotic cells (e.g. DRG cells) even in the presence of a chemotherapeutic agent.

Figure 23:
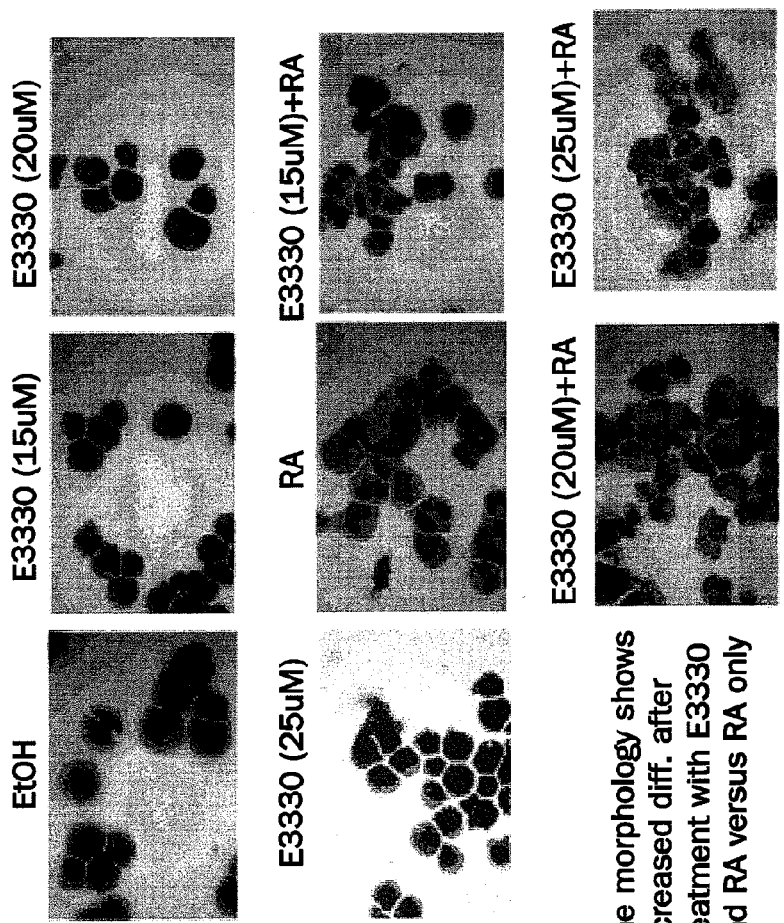
FIG. 23. Effect of E3330 (RN3-3) and retinoic acid on promoting cell differentiation.
Figure 24:
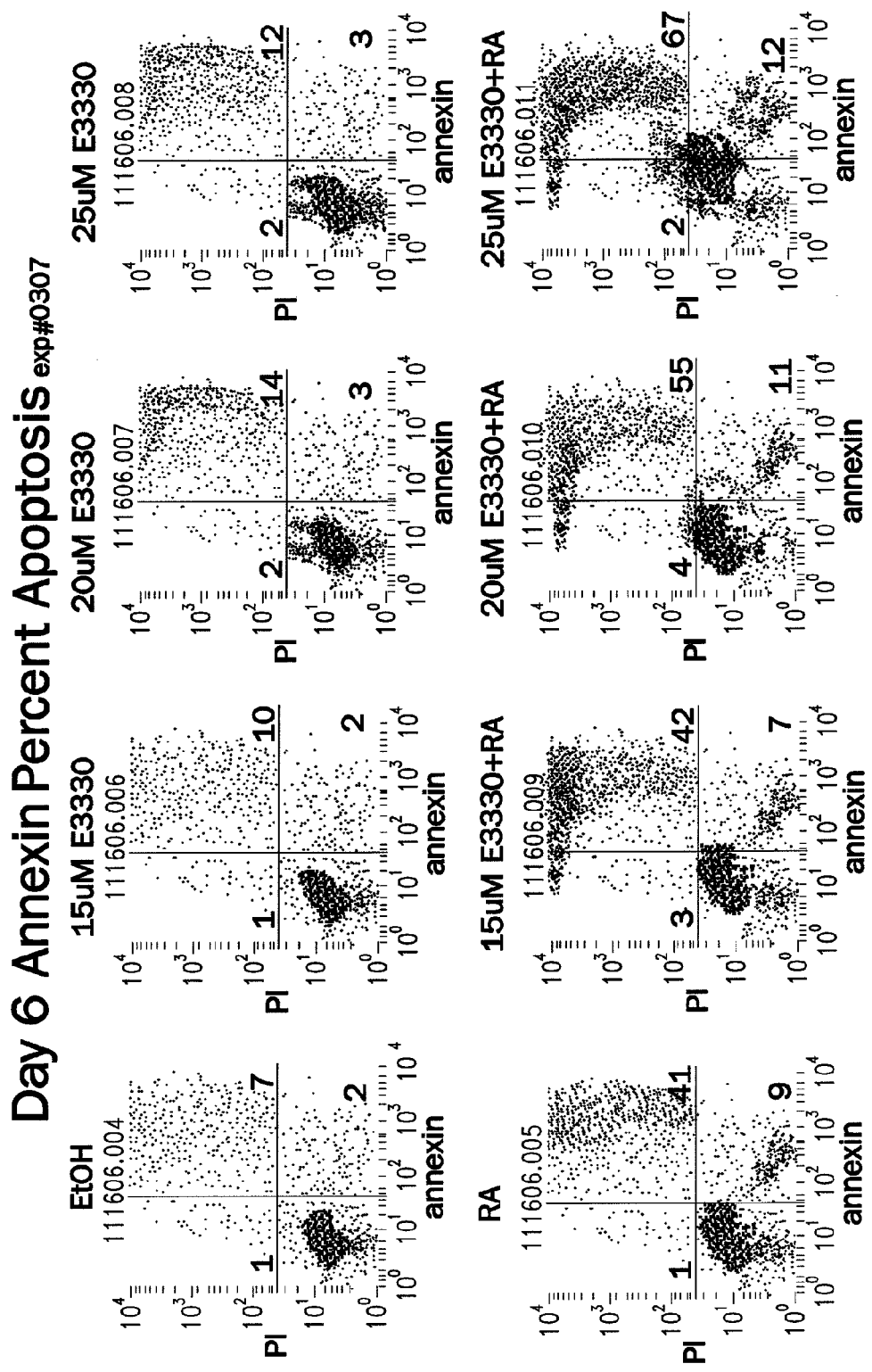
FIG. 24. Apoptosis analysis of HL-60 cells treated as described in FIG. 23 using annexin/PI assay.
Figure 27A:
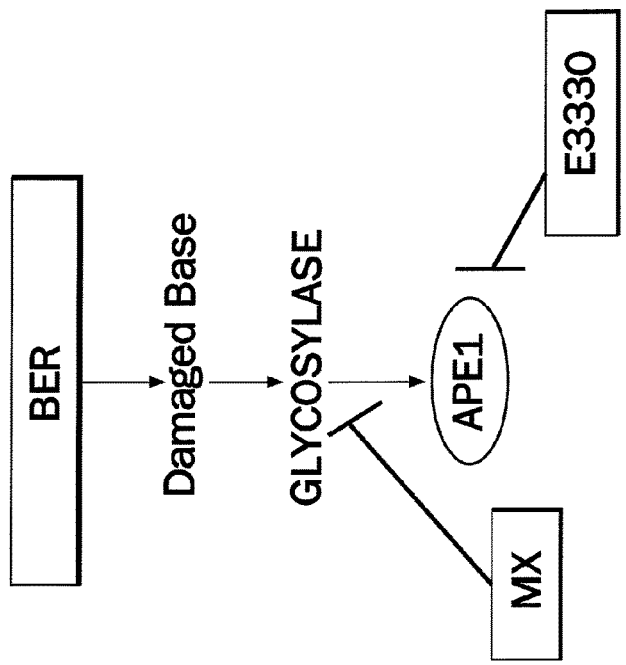
FIGS. 27A-27D. Effect of E3330 (RN3-3) in combination with the small molecule methoxyamine on multiple myeloma cells.
Figure 27B:
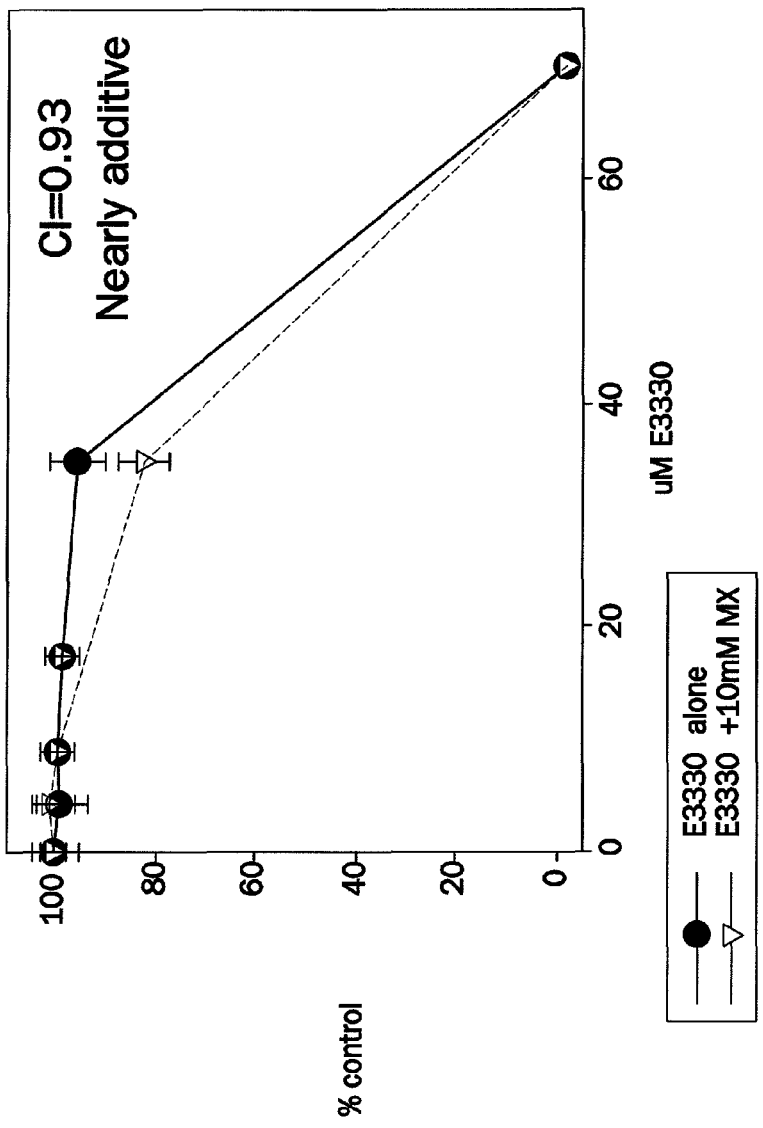
Figure 27C:
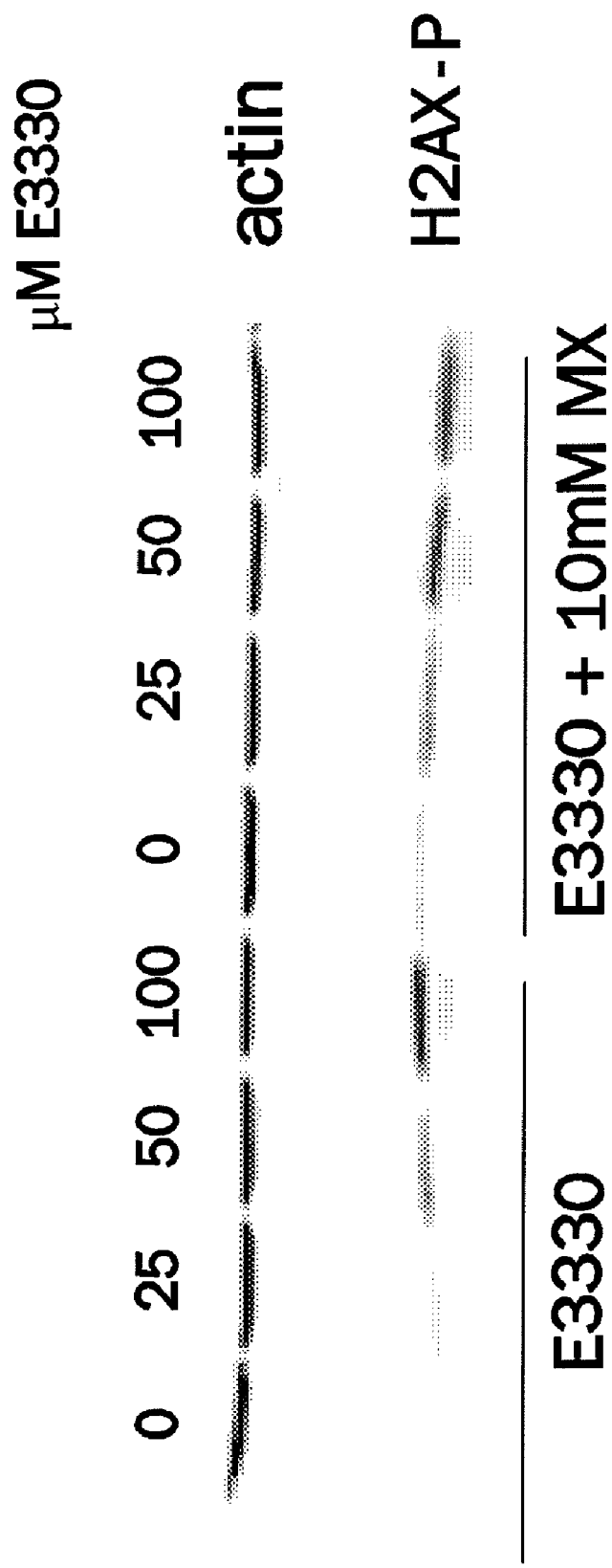
Figure 27D:
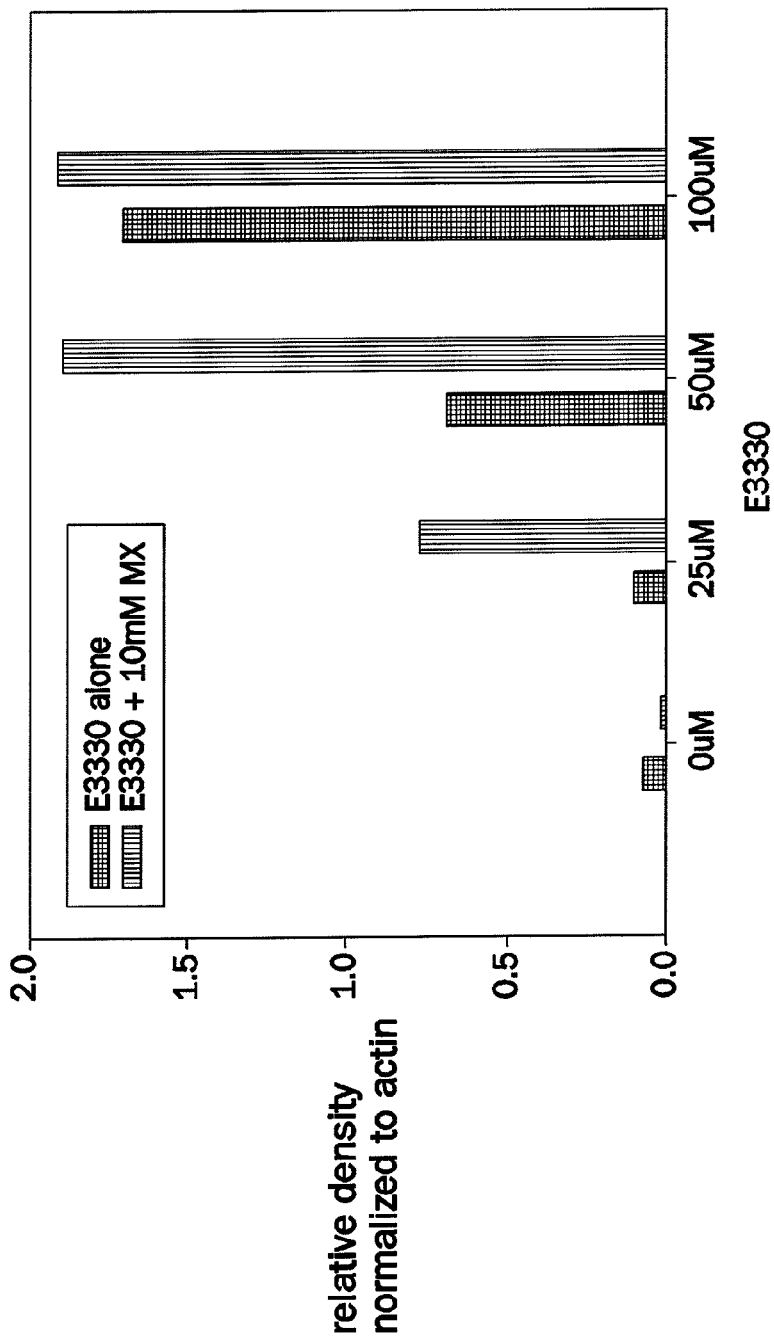

E3330 in combination with Retinoic Acid. E3330 enhanced the effects of retinoic acid on promoting cell differentiation (FIG. 23). HL-60 cells were treated with either vehicle (EtOH; control), E3330, retinoic acid (RA) or E3330 and RA at the concentrations indicated and morphology determined on day six. Morphological analysis indicated an increase in the differentiation of the HL-60 cells treated with E3330 (RN3-3). Apoptosis analysis of HL-60 cells at day 6 revealed that the combination of E3330 and RA showed an increase in the number of cells undergoing apoptosis com-pared to the cells treated with E3330 alone, and about a 1.5 increase compared with RA alone at the 25 uM dose E3330 (FIG. 24).

E3330 enhanced the effect of RA at the 1000 fold lower dose of RA, but resulted in similar levels of differentiation as with the higher doses of RA. CD11, which is a marker for HL-60 differentiation, demonstrated that the addition of E3330 to RA allows for about 1000 fold (3 orders of magnitude) less RA being required to have the same level of differentiation as at higher doses of RA (FIG. 25).

E3330 did not significantly enhance the level of HL-60 cells undergoing apoptosis (annexin/PI assay) at lower doses of RA even though the level of differentiation was greatly enhanced by about 1000 fold (FIG. 26).

These results indicate that E3330 plus RA leads to cell differentiation but not increased apoptosis in these cells and model system at the reduced doses of RA.

E3330 in combination with Methoxyamine-multiple myeloma cells. E3330 in combination with the small molecule methoxyamine enhanced killing of multiple myeloma cells as assayed by MTS (FIGS. 27A-27D). Data was calculated using the CalcuSyn software which is based on the Chou-Talalay algorithm (Chou-Talalay; *Advances in Enzyme Regulation* 22, 27-55). E3330 was either given alone or in combination with methoxyamine.

As an indicator of DNA double stranded breaks (DSBs), the phosphorylation of histone H2AX at Seri 39 was measured with a phosphorylation-specific H2AX antibody from Upstate Cell Signaling Solutions (Waltham, Md.). Cells were treated with E3330 alone or E3330 plus methoxyamine. After drug treatment, exponentially growing cells were harvested, washed in cold PBS, and lysed in about 100 [IL RIM assay buffer as described above. Protein was quantified and electrophoresed in SDS gel-loading buffer on a 12% SDS-polyacrylamide gel. Mouse monoclonal anti-phosphohistone H2AX (about 1:1000) or anti-actin antibody (about 1:1000; as a loading control, LabVision Corp., Neo-Markers, Fremont, Calif.) was used to probe for protein levels as described previously. Bands were detected using a chemiluminescence kit from Roche Applied Biosciences (Indianapolis, Ind.). The bands were visualized using Bio-Rad Chemidoc XRS (Hercules, Calif.) and quantitated using Chemidoc software, Quantity One 4.6.1.

E3330 in combination with Methoxyamine-pancreatic cells. E3330 enhanced the apoptosis inducing effects of methoxyamine in pancreatic tumor. To analyze the cells for apoptosis, cells were plated and allowed to attach overnight. Cells were treated with E3330 alone or with methoxyamine Apoptosis was assayed about 24 and 96 hr following treatment. Cells were trypsinized, pelleted, washed in ice-cold PBS, and resuspended in 1× binding buffer [about 10 mmol/L HEPES/NaOH (pH 7.4), 140 mmol/L NaCl, 2.5 mmol/L $CaCl_2$]. Apoptosis was analyzed using the Alexa Fluor 488 Annexin V from Vybrant Apoptosis Assay kit in combination with propidium iodide (Molecular Probes, Eugene, Oreg.) as described previously Clinical Cancer Research 13, 260-267, Jan. 1, 2007. Cells that were strongly Annexin positive were considered positive for apoptosis. The samples were analyzed by flow cytometry in the Indiana University Cancer Center flow cytometry facility.

Preliminary in-vivo experiments. Preliminary in vivo experiments in mice were performed to explore the safety profile and determine the pharmacokinetic properties of E3330 (FIGS. 19-22).

Figure 19:
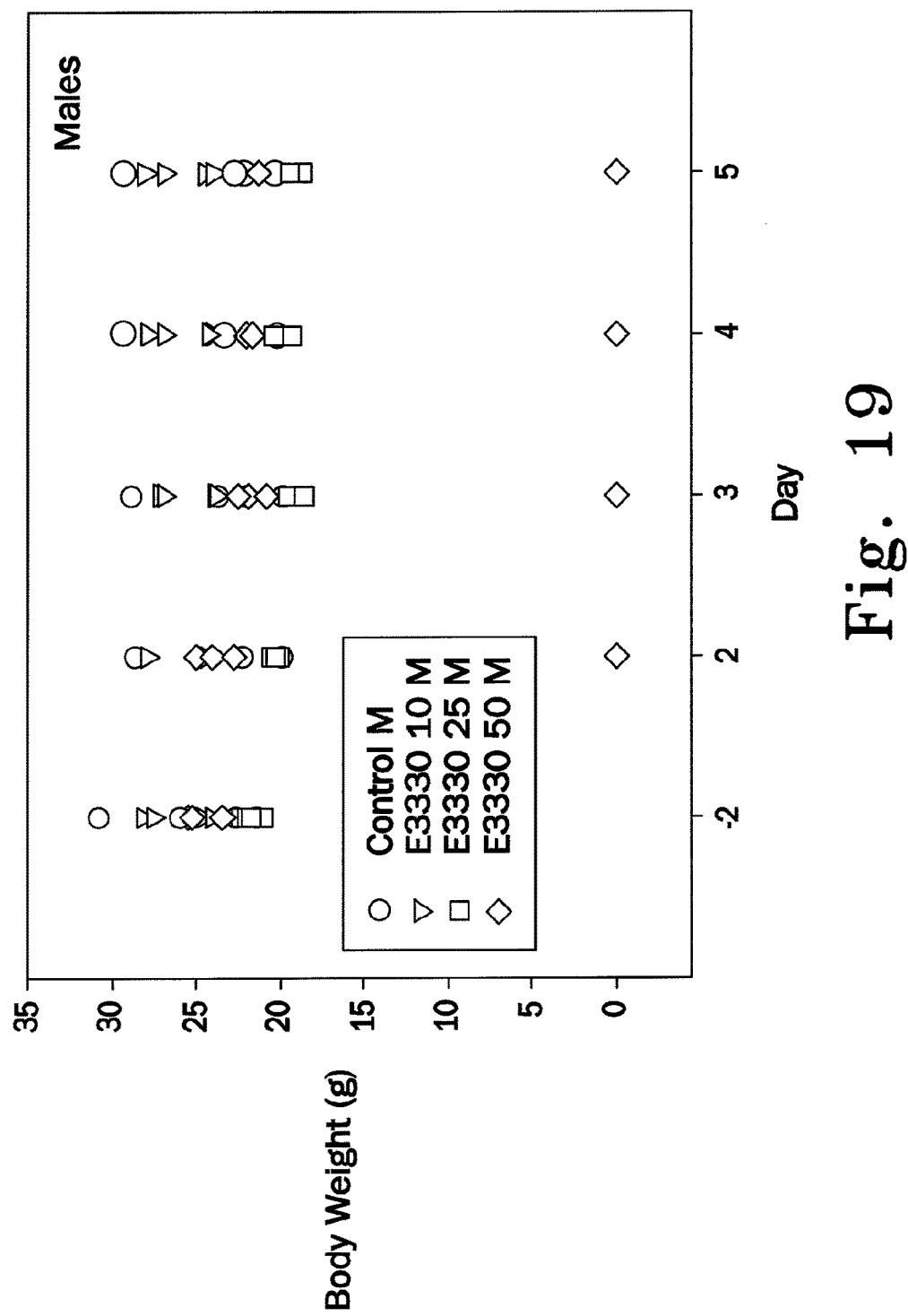
FIG. 19. Body weight in male mice administered E3330 (RN3-3) (0-50 mg/kg).

FIG. 19. Body weight in male mice administered E3330 (RN3-3) (0-50 mg/kg). No mouse toxicity was observed with E3330 (RN3-3) under 50 mg/kg. Mice were treated with RN3-3 (E3330) and weighed either two days before treatment or following treatment with the three doses of compound.

FIG. 20. Survival data of mice treated with RN3-3 (E3330) at various amounts and observed on days 2, 3, 4 or 5 after treatment. The number of surviving mice over the total number are presented as surviving/total.

Figure 21B:
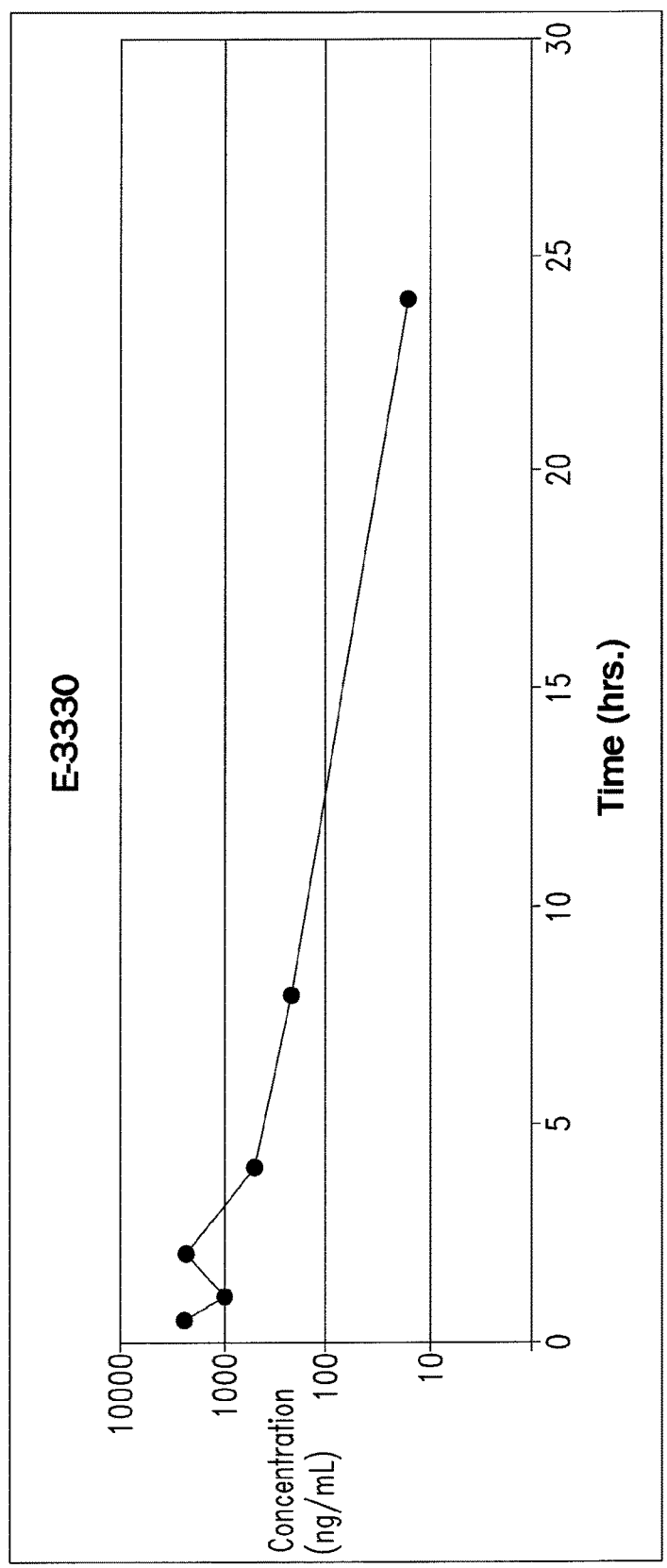

FIGS. 21A & 21B. Pharmacokinetic data of E3330 (RN3-3) over a 24 hr time course experiment. Mice were treated with E3330 (RN3-3) and then the blood concentration detected in the Clinical Pharmacology and Analytical Core (CPAC). The time vs. concentration of E3330 (RN3-3) is plotted (FIG. 21B) and the estimated concentration is shown in the table (FIG. 21A). Three mice were used at each time point and the data represents the mean with SD (not shown) plotted for each time.

FIG. 22. Pharmacokinetic data for E3330 (RN3-3). Data from the survival, weight and PK studies were collected and are shown in this table. The half-life of RN3-3 (E3330) was determined for male, female and combined mice as well as their weight and concentrations.

The invention claimed is:

1. A method for inhibiting a cancer selected from the group consisting of ovarian cancer and breast cancer associated with altered angiogenesis, the method comprising administering to a subject in need thereof an effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, which selectively inhibits the redox function of Ape1/Ref-1 and is effective to inhibit angiogenesis, and at least one additional therapeutic agent selected from the group consisting of melphalan, gemcitabine, cisplatin, and retinoic acid.

2. The method of claim 1 wherein the effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, is from about 10 μM to about 100 μM.

3. The method of claim 1 wherein the effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, is from about 40 μM to about 60 μM.

4. A method for inhibiting a cancer selected from the group consisting of ovarian cancer and breast cancer, the method comprising administering to a subject in need thereof an effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, which selectively inhibits the redox function of Ape1/Ref-1 and is effective to inhibit angiogenesis, and inhibits tumor cell growth and administering at least one additional therapeutic agent selected from the group consisting of melphalan, cisplatin, gemcitabine and retinoic acid to the subject.

5. The method of claim 4 wherein the effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, is from about 10 μM to about 100 μM.

6. The method of claim 4 wherein the effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, is from about 40 μM to about 60 μM.

7. A method for inhibiting a cancer selected from the group consisting of ovarian cancer and breast cancer associated with altered angiogenesis, the method comprising administering to a subject in need thereof an effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, which selectively inhibits the redox function of Ape1/Ref-1 and is effective to inhibit angiogenesis, in combination with bevacizumab.

8. The method of claim 7 wherein the effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, is from about 10 μM to about 100 μM.

9. The method of claim 7 wherein the effective amount of 3-[(5-(2,3-dimethoxy-6-methyl 1,4-benzoquinoyl)]-2-nonyl-2-propenoic acid, a pharmaceutically acceptable salt or a pharmaceutically acceptable solvate thereof, is from about 40 μM to about 60 μM.

* * * * *

UNITED STATES PATENT AND TRADEMARK OFFICE
CERTIFICATE OF CORRECTION

PATENT NO. : 10,058,523 B2  
APPLICATION NO. : 14/690973  
DATED : August 28, 2018  
INVENTOR(S) : Mark R. Kelley Page 1 of 1

It is certified that error appears in the above-identified patent and that said Letters Patent is hereby corrected as shown below:

In the Specification

At Column 4, Lines 1-9 should read:

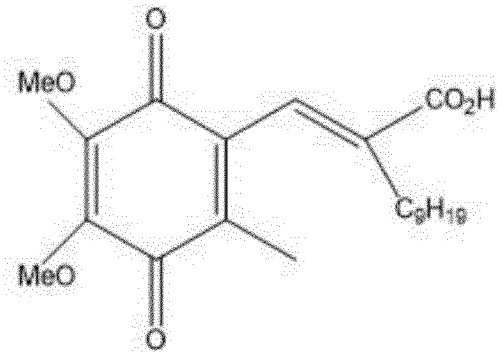

Signed and Sealed this  
Twenty-first Day of January, 2020

Andrei Iancu  
*Director of the United States Patent and Trademark Office*